(12) United States Patent
Nakamura et al.

(10) Patent No.: US 10,812,356 B2
(45) Date of Patent: Oct. 20, 2020

(54) MEASUREMENT RESULT MANAGEMENT APPARATUS AND MEASUREMENT RESULT MANAGEMENT METHOD

(71) Applicant: FUJITSU LIMITED, Kawasaki-shi, Kanagawa (JP)

(72) Inventors: Yosuke Nakamura, Kawasaki (JP); Kazuaki Nimura, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 65 days.

(21) Appl. No.: 16/207,263

(22) Filed: Dec. 3, 2018

(65) Prior Publication Data

US 2019/0173768 A1 Jun. 6, 2019

(30) Foreign Application Priority Data

Dec. 5, 2017 (JP) .................. 2017-233564

(51) Int. Cl.
| | |
|---|---|
| H04L 12/26 | (2006.01) |
| H04L 29/08 | (2006.01) |
| G06F 1/16 | (2006.01) |
| H04W 4/02 | (2018.01) |
| G16H 40/67 | (2018.01) |

(52) U.S. Cl.
CPC .............. *H04L 43/08* (2013.01); *G06F 1/163* (2013.01); *H04L 67/12* (2013.01); *H04L 67/18* (2013.01); *H04W 4/023* (2013.01); *G16H 40/67* (2018.01)

(58) Field of Classification Search
CPC ......... H04L 43/08; H04L 67/12; H04L 67/18; G06F 1/163; H04W 4/023; G16H 40/67
See application file for complete search history.

(56) References Cited

U.S. PATENT DOCUMENTS

| | | | |
|---|---|---|---|
| 2008/0027679 A1* | 1/2008 | Shklarski | G16H 40/67 |
| | | | 702/182 |
| 2014/0207489 A1 | 7/2014 | Wartena et al. | |
| 2014/0259133 A1 | 9/2014 | Diaz et al. | |
| | (Continued) | | |

FOREIGN PATENT DOCUMENTS

JP 2011-018956 1/2011

OTHER PUBLICATIONS

EPOA—Office Action of European Patent Application No. 18208246.1 dated Oct. 10, 2019.

(Continued)

*Primary Examiner* — Arvin Eskandarnia
(74) *Attorney, Agent, or Firm* — Fujitsu Patent Center

(57) ABSTRACT

A measurement result management apparatus includes one or more memories, and one or more processors coupled to the one or more memories and the one or more processors configured to acquire, from a plurality of devices worn by a plurality of users, location information indicating locations of the plurality of devices, perform, in response to acquisition of a first measurement result including a first measurement time from a first measurement apparatus, a selection of a first device from the plurality of devices in accordance with a location of the first measurement apparatus, the first measurement time, and the location information, and store the first measurement result in association with the selected first device in the one or more memories.

19 Claims, 21 Drawing Sheets

(56) References Cited

U.S. PATENT DOCUMENTS

| | | | | |
|---|---|---|---|---|
| 2016/0150361 A1* | 5/2016 | Zhu | ............... | G08G 1/0112 |
| | | | | 455/456.1 |
| 2016/0363479 A1* | 12/2016 | Dumont | ............... | G01J 1/0403 |
| 2017/0032101 A1* | 2/2017 | Skoda | ............... | G06F 19/3456 |
| 2017/0069193 A1* | 3/2017 | Schmidt | ............... | G08B 21/14 |
| 2019/0320403 A1* | 10/2019 | Zhang | ............... | H04W 24/10 |

OTHER PUBLICATIONS

EESR—Extended European Search Report of European Patent Application No. 18208246.1 dated Mar. 28, 2019.

* cited by examiner

FIG. 4A

| DEVICE ID | USER |
|---|---|
| 001 | A |
| 002 | B |
| 003 | C |

FIG. 4B

| DEVICE ID | DATE AND TIME | LOCATION |
|---|---|---|
| ... | ... | ... |
| 001 | 5/10/2017 10:00:00 | 100,100 |
| 001 | 5/10/2017 10:00:05 | 150,110 |
| 002 | 5/10/2017 10:00:03 | 150,65 |
| 003 | 5/10/2017 10:00:03 | 250,100 |
| ... | ... | ... |

FIG. 4C

| MEASUREMENT APPARATUS ID | CONDITION 1 | CONDITION 2 | ... | INSTALLATION LOCATION |
|---|---|---|---|---|
| A0001 | DISTANCE<10 | DISTANCE DURING 30 SECONDS < 10 | ... | 150,70 |
| ... | ... | ... | ... | ... |

FIG. 5A

| DATE AND TIME | MEASUREMENT APPARATUS ID | MEASUREMENT RESULT | USER |
|---|---|---|---|
| ... | ... | ... | ... |
| 5/10/2017 10:00:03 | A001 | 65 | |
| ... | ... | ... | ... |

FIG. 5B

| DATE AND TIME | MEASUREMENT APPARATUS ID | MEASUREMENT RESULT | USER |
|---|---|---|---|
| ... | ... | ... | ... |
| 5/10/2017 10:00:03 | A001 | 65 | B |
| ... | ... | ... | ... |

FIG. 9A

| DEVICE ID | USER | READING UNIT | NOTIFICATION |
|---|---|---|---|
| 001 | – | NOT PROVIDED | LED |
| 002 | – | NOT PROVIDED | LED |
| 003 | – | PROVIDED | LED |

FIG. 9B

| DEVICE ID | DATE AND TIME | LOCATION |
|---|---|---|
| ... | ... | ... |
| 001 | 5/10/2017 10:00:00 | 100,100 |
| 001 | 5/10/2017 10:00:05 | 150,110 |
| 002 | 5/10/2017 10:00:03 | 150,65 |
| 003 | 5/10/2017 10:00:03 | 250,100 |
| ... | ... | ... |

FIG. 9C

| MEASUREMENT APPARATUS ID | CONDITION 1 | CONDITION 2 | ... | INSTALLATION LOCATION |
|---|---|---|---|---|
| A0001 | DISTANCE < 10 | DISTANCE DURING 30 SECONDS < 10 | ... | 150,70 |
| ... | ... | ... | ... | ... |

FIG. 10A

| DATE AND TIME | MEASUREMENT APPARATUS ID | MEASUREMENT RESULT | USER |
|---|---|---|---|
| ... | ... | ... | ... |
| 5/10/2017 10:00:03 | A001 | 65 | |
| ... | ... | ... | ... |

FIG. 10B

| READER DEVICE ID | NOTIFICATION | LOCATION |
|---|---|---|
| SP-01 | LED | 170,80 |
| SP-02 | LED | 250,100 |
| ... | ... | ... |

FIG. 15A

| USER | DATE | START | END | CONTENT |
|------|------|-------|-----|---------|
| A | 10/18/2017 | 10:00 | 12:00 | HEALTH CHECK |
| A | 10/18/2017 | 13:00 | 14:00 | MEETING |
| A | 10/18/2017 | 14:30 | 17:00 | BUSINESS TRIP |
| ... | ... | ... | ... | ... |

FIG. 15B

| USER | POSSESSED DEVICE | STATE |
|------|------------------|-------|
| A | PC | LOGIN |
| A | SMARTPHONE | POWER OFF |
| ... | ... | ... |

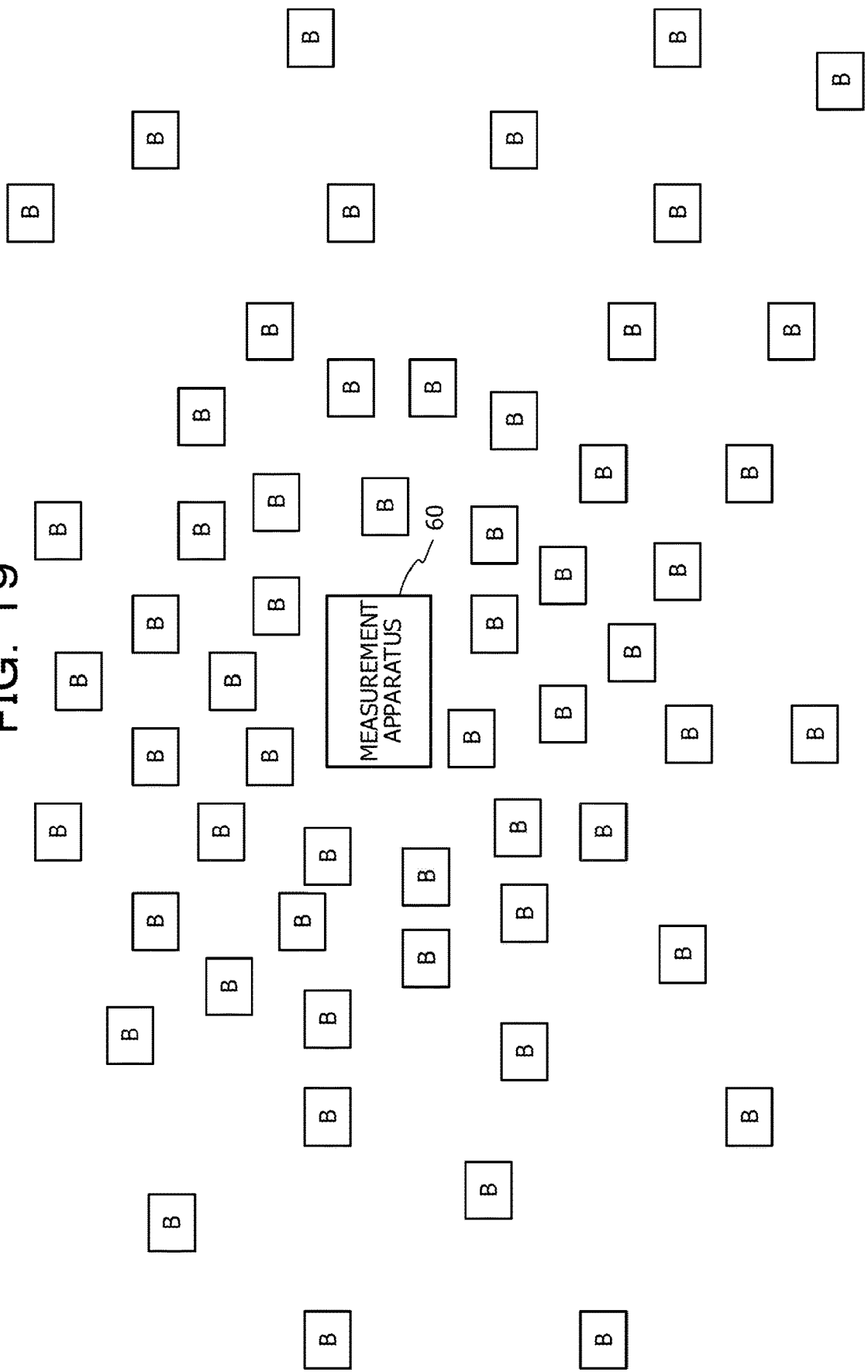

MEASUREMENT RESULT MANAGEMENT APPARATUS AND MEASUREMENT RESULT MANAGEMENT METHOD

CROSS-REFERENCE TO RELATED APPLICATION

This application is based upon and claims the benefit of priority of the prior Japanese Patent Application No. 2017-233564, filed on Dec. 5, 2017, the entire contents of which are incorporated herein by reference.

FIELD

The embodiments discussed herein are related to a technology of managing a measurement result.

BACKGROUND

In systems of the related art that use sensing data, a technology of automatically associating a sensed object with sensing data is known. In the related art, when sensing data acquired by the same sensor at the same time is received in a plurality of object-identifying apparatuses, an object-identifying apparatus to be associated with the sensing data is selected in accordance with the level of a received signal in each of the object-identifying apparatuses. In such a technology, when an object-identifying apparatus and a user are associated with each other in advance, the user and sensing data may be associated with each other.

The related art is disclosed in, for example, Japanese Laid-open Patent Publication No. 2011-18956.

SUMMARY

According to an aspect of the embodiments, a measurement result management apparatus includes one or more memories, and one or more processors coupled to the one or more memories and the one or more processors configured to acquire, from a plurality of devices worn by a plurality of users, location information indicating locations of the plurality of devices, perform, in response to acquisition of a first measurement result including a first measurement time from a first measurement apparatus, a selection of a first device from the plurality of devices in accordance with a location of the first measurement apparatus, the first measurement time, and the location information, and store the first measurement result in association with the selected first device in the one or more memories.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4A is a diagram illustrating an example of a wearable device table according to the first embodiment;

FIG. 4B is a diagram illustrating an example of a wearable device location DB according to the first embodiment;

FIG. 4C is a diagram illustrating an example of a measurement apparatus table according to the first embodiment;

FIG. 5A and FIG. 5B are diagrams illustrating an example of a measurement result DB according to the first embodiment;

FIG. 9A is a diagram illustrating an example of a wearable device table according to the second embodiment;

FIG. 9B is a diagram illustrating an example of a wearable device location DB according to the second embodiment, FIG. 9C is a diagram illustrating an example of a measurement apparatus table according to the second embodiment;

FIG. 10A is a diagram illustrating an example of a measurement result DB according to the second embodiment;

FIG. 10B is a diagram illustrating an example of a reader device table according to the second embodiment;

FIG. 15A is a diagram illustrating an example of a schedule DB according to the third embodiment;

FIG. 15B is a diagram illustrating an example of a possessed device table according to the third embodiment;

FIG. 19 is a diagram illustrating a method of arranging beacons according to the modified example;

DESCRIPTION OF EMBODIMENTS

In conventional technology, when the object-identifying apparatuses described above (for example, gateways) and users are not associated with each other in one-to-one manner, for example, it is difficult to automatically associate sensing data with the user when the gateway is a fixed-type apparatus and shared by a plurality of users.

First Embodiment

Hereinafter, a first embodiment of an information processing system will be described in detail in accordance with FIG. 1 to FIG. 7. An information processing system 100 according to the first embodiment is a system that, when a user wears a wearable device 70 and uses a measurement apparatus 60 such as a sphygmomanometer or a weighing scale, automatically associates data obtained from the measurement apparatus 60 (measurement result) with the user corresponding to the measurement result.

Figure 1:
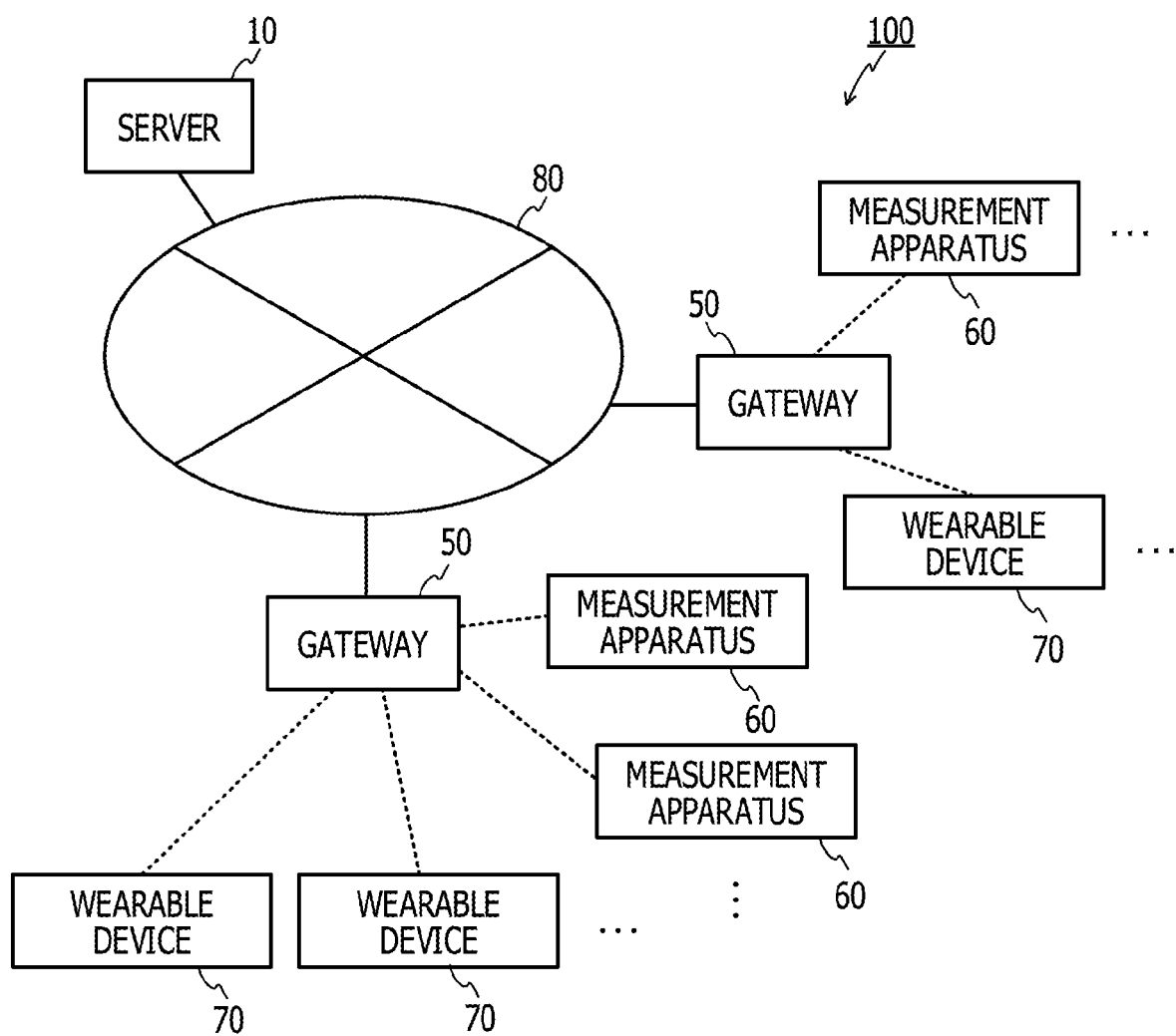
FIG. 1 is a diagram schematically illustrating a configuration of an information processing system according to a first embodiment.

FIG. 1 schematically illustrates a configuration of the information processing system 100. As illustrated in FIG. 1, the information processing system 100 includes a server 10 as a measurement result management apparatus, gateways 50, wearable devices 70 as devices, and measurement apparatuses 60 as apparatuses. The server 10 and the gateways 50 are connected to a network 80 such as the Internet. Further, each gateway 50 is able to communicate wirelessly with the wearable devices 70 and the measurement apparatuses 60 present within a predetermined range from the gateway 50.

Figure 2A:
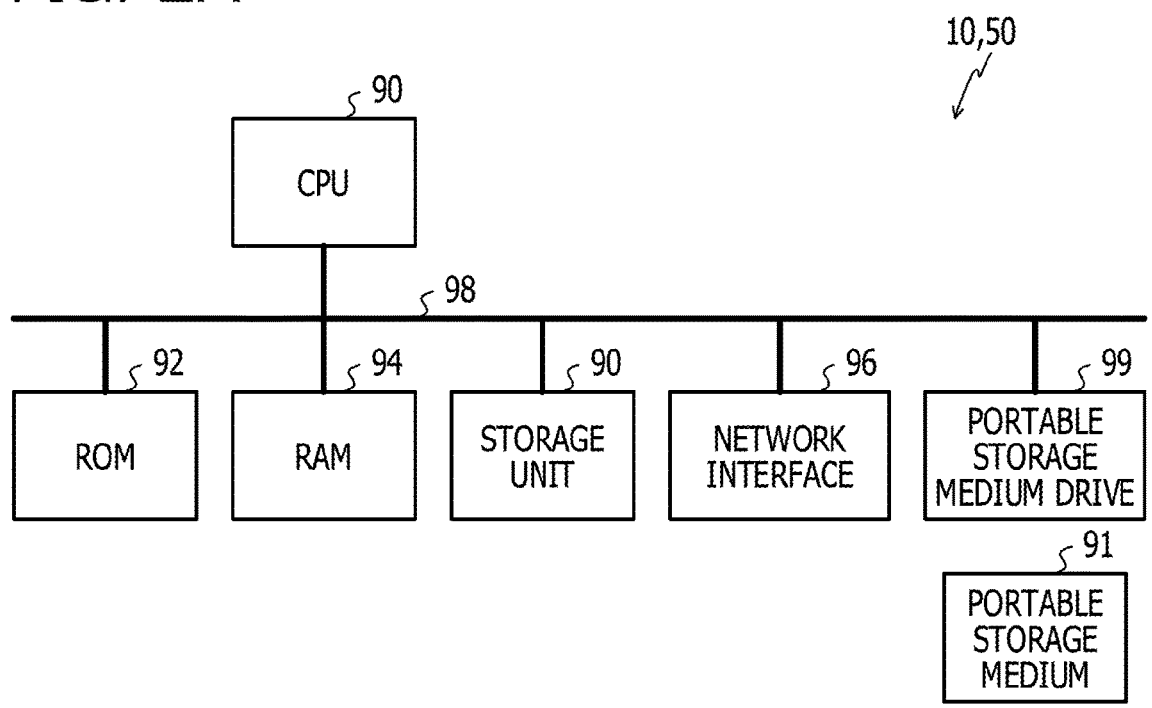
FIG. 2A is a diagram illustrating a hardware configuration of a server and a gateway.
Figure 3:
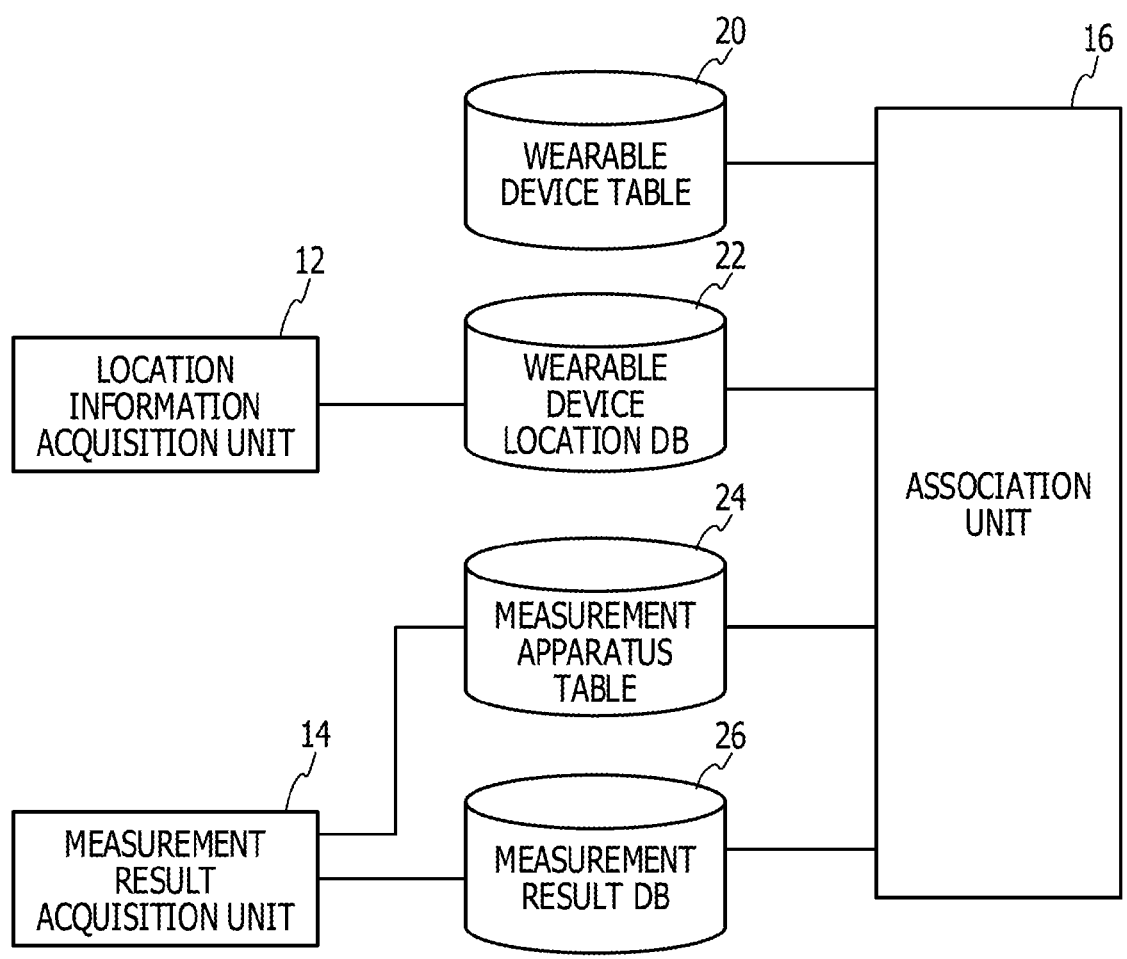
FIG. 3 is a function block diagram according to the first embodiment.

The server 10 has a hardware configuration as illustrated in FIG. 2A. As illustrated in FIG. 2A, the server 10 has a central processing unit (CPU) 90, a read-only memory (ROM) 92, a random access memory (RAM) 94, a storage unit (for example, a hard disk drive (HDD)) 96, a network interface 97, and a portable storage medium drive 99. Each of these components of the server 10 is connected to a bus 98. In the server 10, when a program stored in the ROM 92 or the storage unit 96 (for example, a measurement result management program including a plurality of programs) or a program (for example, a measurement result management program including a plurality of program instructions) read from a portable storage medium 91 by the portable storage medium drive 99 is executed by the CPU 90, functions of respective units illustrated in FIG. 3 are implemented. Note that the function block diagram of FIG. 3 will be described later in detail. In the embodiment, the CPU is an example of a processor.

The gateway 50 may be, for example, a fixed gateway or a portable apparatus such as a smartphone. The gateway 50 has a hardware configuration as illustrated in FIG. 2A, similar to that of the server 10. Note that some suitable component may be added to the configuration in FIG. 2A in accordance with the type of the gateway 50. The gateway 50 mediates between the wearable device 70 or the measurement apparatus 60 and the server 10 for data transactions.

Figure 2B:
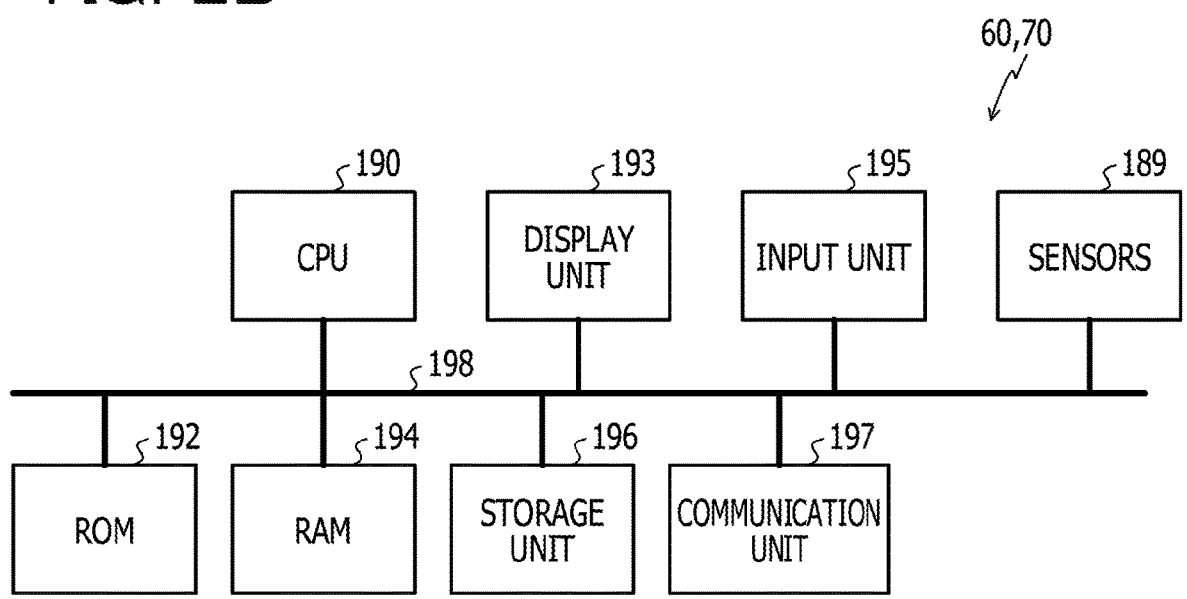
FIG. 2B is a diagram illustrating a hardware configuration of a wearable device and a measurement apparatus.

Each of the wearable devices 70 is a device of a wrist watch type, a wristband type, a ring type, or the like that may be worn on an arm, a wrist, or the like of the user. The wearable device 70 has a hardware configuration as illustrated in FIG. 2B. As illustrated in FIG. 2B, the wearable device 70 has a CPU 190, a ROM 192, a RAM 194, a storage unit (for example, a solid state drive (SSD)) 196, a communication unit 197, a display unit 193, an input unit 195, sensors 189, and the like. Each of these components of the wearable device 70 is connected to a bus 198. The sensors 189 include a global positioning system (GPS) sensor, an acceleration sensor, or the like, for example. The wearable device 70 transmits, to the server 10 via the gateway 50, location information detected by the GPS sensor or acceleration information detected by the acceleration sensor.

Each of the measurement apparatuses 60 is an apparatus such as a sphygmomanometer or a weighing scale used by the user. The measurement apparatus 60 has a hardware configuration, as illustrated in FIG. 2B, similar to that of the wearable device 70. The sensors 189 contained in the measurement apparatus 60 may include a sensor used for measuring a blood pressure (pressure sensor or the like), a sensor used for measuring weight (weight sensor or the like), a sensor used for measuring body fat, and a GPS sensor, for example. The measurement apparatus 60 generates measurement data (a measurement result) from values detected by using the sensors 189 every time a measurement ends. Further, the measurement apparatus 60 transmits a measurement result to the server 10 via the gateway 50 every time a measurement result is generated. Further, the measurement apparatus 60 transmits location information to the server 10 every time the location information measured by the GPS sensor changes.

FIG. 3 illustrates a function block diagram of the server 10. As illustrated in FIG. 3, when the CPU 90 executes a program, the server 10 functions as a location information acquisition unit 12 as a first acquisition unit, a measurement result acquisition unit 14 as a second acquisition unit, and an association unit 16. Note that FIG. 3 illustrates a wearable device table 20, a wearable device location DB 22, a measurement apparatus table 24 as a storage unit, and a measurement result DB 26 that are stored in the storage unit 96 or the like.

The location information acquisition unit 12 acquires location information transmitted from the wearable devices 70 and stores the acquired location information in the wearable device location DB 22. The wearable device location DB 22 has the data structure as illustrated in FIG. 4B. Specifically, the wearable device location DB 22 has fields of "device ID", "date and time", and "location" as illustrated in FIG. 4B. That is, the location information of each of the wearable devices 70 is stored together with a detected date and time in the wearable device location DB 22 in association with each device ID of the wearable devices 70. Note that the location (coordinate values) of the wearable device 70 on a coordinate system set with respect to a predetermined location as an origin is stored in the location field. Without being limited thereto, however, longitude and latitude values may be stored in the location field.

The measurement result acquisition unit 14 acquires measurement data (measurement result) transmitted from the measurement apparatuses 60 and stores the transmitted measurement data in the measurement result DB 26. As illustrated in FIG. 5A, the measurement result DB 26 has fields of "date and time", "measurement apparatus ID", "measurement result", and "user". That is, in the measurement result DB 26, a measurement result and a measurement date and time are stored in association with the measurement apparatus ID of each measurement apparatus 60. Further, when a user is associated with a measurement result as a result of the process in the association unit 16 described later, information of the associated user is stored in the user field of the measurement result DB 26.

The association unit 16 identifies the user to which a measurement result acquired from the measurement apparatus corresponds and then associates the measurement result with the identified user. When performing association, the association unit 16 refers to the wearable device table 20 and the measurement apparatus table 24 rather than the wearable device location DB 22 and the measurement result DB 26 described above.

As illustrated in FIG. 4A, the wearable device table 20 is a table in which information on the user wearing the wearable device 70 is stored, and data of the "device ID" field and the "user" field are stored in association with each other. As illustrated in FIG. 4C, the measurement apparatus table 24 is a table in which information on the measurement apparatus 60 is stored, and condition 1, condition 2, installation location, and the like are stored in association with the measurement apparatus ID. The installation location corresponds to location coordinates at which the measurement apparatus 60 is installed. Note that the measurement result acquisition unit 14 stores the location information transmitted from the measurement apparatus 60 in the measurement apparatus table 24 as an installation location. A condition for identifying the user who used the measurement apparatus 60 is stored in the condition 1 or condition 2 field. That is, the condition 1 and the condition 2 define a range of values or the like which are likely to be detected by the sensors 189 of the wearable device 70 worn by the user when the user uses the measurement apparatus 60. Therefore, when the wearable device 70 outputs a value which satisfies the condition 1 or the condition 2 when the measurement apparatus 60 outputs a measurement result, there is a high likelihood that the user wearing the wearable device 70 of interest used the measurement apparatus 60 in the past.

(Process in Server 10)

Figure 6:
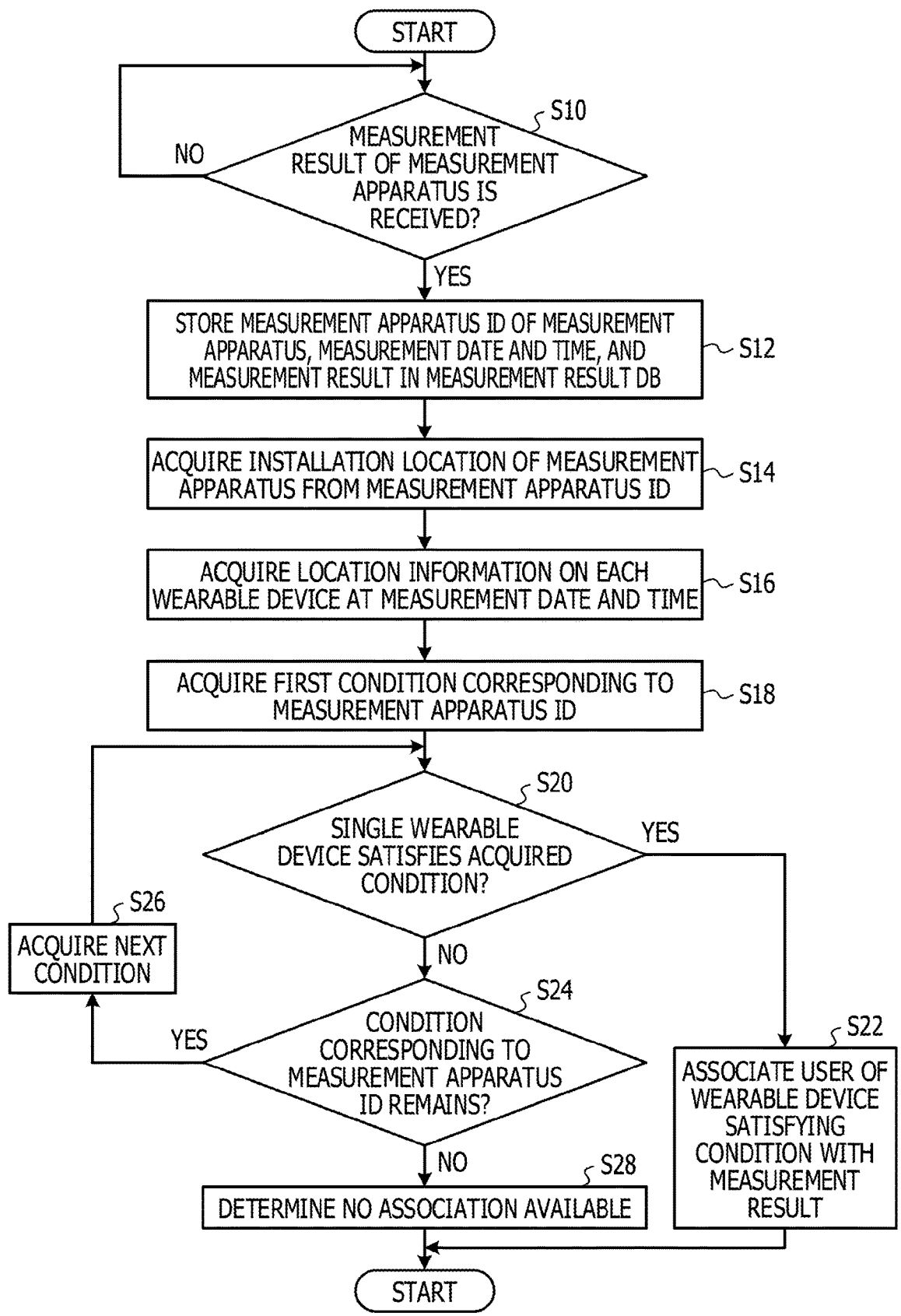
FIG. 6 is a flowchart illustrating a process of the server according to the first embodiment.
Figure 7:
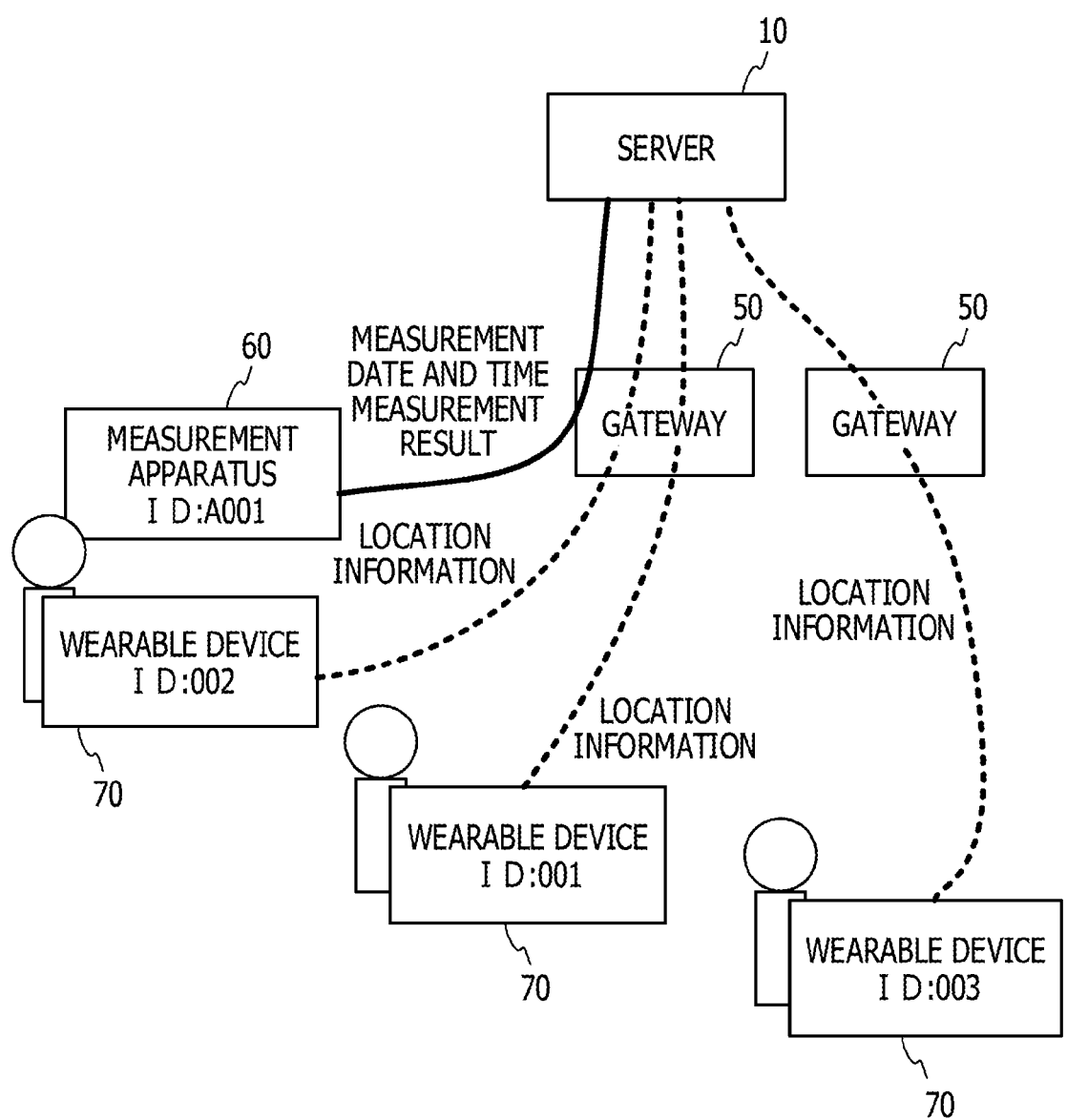
FIG. 7 is a diagram illustrating transaction of data in the first embodiment.

Next, the process in the server 10 will be described in detail in accordance with the flowchart of FIG. 6 and with reference to other drawings. Before the process illustrated in FIG. 6 is started, it is assumed that information on each of the wearable devices 70 (information on the user wearing the wearable device 70) is stored in the wearable device table 20 and that information on each of the measurement apparatuses 60 (information on the condition or the installation location of the measurement apparatus 60) is stored in the measurement apparatus table 24. Further, location information is transmitted from the wearable device 70 at predetermined time intervals (see the bold dashed line in FIG. 7), and the location information acquisition unit 12 stores the received location information in the wearable device location DB 22 permanently.

Once the process illustrated in FIG. 6 is started, first, in step S10, the measurement result acquisition unit 14 stands by until receiving a measurement result from the measurement apparatus 60. That is, when a measurement result is transmitted from the measurement apparatus 60 (ID=A001), for example, the measurement result acquisition unit 14 proceeds to step S12, as illustrated by a bold solid line in FIG. 7.

After proceeding to step S12, the measurement result acquisition unit 14 stores, in the measurement result DB 26, the measurement apparatus ID (A001) of the measurement apparatus 60, the measurement date and time, and the measurement result.

Next, in step S14, the association unit 16 acquires the measurement apparatus ID (A001) newly stored in the measurement result DB 26 and acquires, from the measurement apparatus table 24, information on the location (installation location) where the measurement apparatus 60 corresponding to the acquired measurement apparatus ID is installed. In the example in FIG. 4C, an installation location "150, 70" is acquired.

Next, in step S16, the association unit 16 acquires a measurement date and time newly stored in the measurement result DB 26 (2017/5/10 10:00:03 in the example in FIG. 5A) and acquires location information of each of the wearable devices 70 obtained at the acquired measurement date and time. That is, the location of each wearable device 70 at the time of measurement in the measurement apparatus 60 is identified. When there is a wearable device 70 having no location information obtained at a measurement date and time, the location of the wearable device 70 is estimated in accordance with location information obtained before or after the measurement date and time. Specifically, as illustrated in FIG. 4B, it is assumed that, when the date and time of measurement of the location of the wearable device 70 having the device ID=001 is "2017/5/10 10:00:00" and "2017/5/10 10:00:05", the measurement date and time of the measurement apparatus 60 is assumed to be "2017/5/10 10:00:03". In this case, a location "130, 106" is calculated as an internal point on the line connecting the location "100, 100" at the date and time "2017/5/10 10:00:00" and the location "150, 110" at the date and time "2017/5/10 10:00:05" by dividing the line at a ratio of 3:2. The location "130, 106" is estimated as a location of the wearable device 70 at the time of measurement in the measurement apparatus 60.

Next, in step S18, the association unit 16 acquires the first condition corresponding to the measurement apparatus ID. For example, when the measurement apparatus ID is A001, the association unit 16 acquires the first condition 1 "distance<10". Note that the condition "distance<10" is a condition that is used to identify the wearable device 70 of a user who is present near the measurement apparatus 60 when the measurement result is output from the measurement apparatus 60.

Next, in step S20, the association unit 16 determines whether or not the number of wearable devices satisfying the acquired condition is 1. That is, the distance between each wearable device 70 and the measurement apparatus 60 is calculated from the installation location of the measurement apparatus 60 acquired in step S14 and the location of each wearable device 70 acquired in step S16, and it is determined whether or not the number of the wearable devices 70 present within a distance of 10 meters is 1. If the determination in step S20 is YES, the process proceeds to step S22.

When proceeding to step S22, the association unit 16 identifies the user of the wearable device 70 satisfying the condition in the wearable device table 20 (see FIG. 4A) and associates the user with the measurement result. For example, when the ID of the wearable device 70 satisfying the condition is 002, the user wearing the wearable device 70 having ID=002 is identified as "B" by referencing to the wearable device table 20, and the user B and the measurement result are associated with each other. In such a case, the association unit 16 stores information on the identified user in the "user" field in the measurement result DB 26 illustrated in FIG. 5A (see user "B" in FIG. 5B). Then, the entire process in FIG. 6 ends. "B"

On the other hand, if the determination in step S20 is NO, that is, when one of the wearable devices 70 (user) is not identified for the acquired condition, the association unit 16 proceeds to step S24. When proceeding to step S24, the association unit 16 refers to the measurement apparatus table 24 and determines whether or not there remains another condition corresponding to the measurement apparatus ID. If the determination thereof is YES, the association unit 16 proceeds to step S26 and, after acquiring the next condition, returns to step S20. In the example in FIG. 4C, the association unit 16 may acquire "distance during 30 seconds<10" as the next condition 2. In this case, in step S20, the association unit 16 determines whether or not the number of the wearable devices 70 that have been present within 10 meters from the measurement apparatus 60 during 30 seconds before the measurement result is obtained is only 1. Note that the condition "distance during 30 seconds<10" is a condition that identifies the wearable device 70 of the user who has used the measurement apparatus 60, such as when a stationary user continues to use the measurement apparatus 60 for at least 30 seconds. If the determination in step S20 is YES, the entire process in FIG. 6 ends after step S22 is performed as described above. On the other hand, if the determination in step S20 is NO, the process proceeds to step S24.

If the determination in step S20 is NO and while the determination in step S24 continues to be YES, the process and determination of steps S26, S20, and S24 are repeatedly performed. However, after all the conditions have been acquired and if the determination in step S24 is NO, the association unit 16 proceeds to step S28. The association unit 16 then determines in step S28 that no association is available. Then, the entire process in FIG. 6 ends. Note that when it is determined that no association is available, the association unit 16 may notify the manager of the server 10 or the like that no association is available. In such a case, the manager may associate the measurement result with the user by manual entry.

Note that after the end of the process in FIG. 6, the process in FIG. 6 is re-started. That is, the server 10 repeatedly performs the process in steps S12 to S28 in FIG. 6 each time a measurement result is received from the measurement apparatus 60.

As described above in detail, according to the first embodiment, the location information acquisition unit 12 acquires a measurement result (location information in the first embodiment) of the sensors 189 from the plurality of wearable devices 70 worn by a plurality of users and associated with respective users in the wearable device table 20, and the measurement result acquisition unit 14 acquires the measurement result of the measurement apparatus 60 used by the user. The association unit 16 then identifies the wearable device 70 of the user who used the measurement apparatus 60 in accordance with the measurement result (location information) of each wearable device 70 corresponding to a measurement date and time of the measurement result acquired by the measurement result acquisition unit 14 and associates the measurement result with the user who is associated with the identified wearable device 70. As discussed above, in the first embodiment, the user who used the measurement apparatus 60 is identified in accordance with the measurement result (location information) of the wearable device 70 obtained at the time the measurement apparatus 60 was used, it is possible to automatically associate the user with the measurement result of the measurement apparatus 60. Thus, since a user and a measurement result do not have to be associated with each other by manual entry or the like, the load of associating the user with the measurement result of the measurement apparatus 60 (load on the user or a person who handles the measurement result) may be reduced.

Further, in the first embodiment, the association unit 16 stores a condition for each measurement apparatus 60 in the measurement apparatus table 24 and identifies the wearable device 70 satisfying the condition as the wearable device 70 worn by the user who used the measurement apparatus 60. Thereby, the wearable device 70 worn by the user who used the measurement apparatus 60 may be identified in a simple manner by using a process of identifying the wearable device 70 satisfying the condition stored in the measurement apparatus table 24. It is therefore possible to associate the user and the measurement result of the measurement apparatus 60 in a simple manner.

Further, in the first embodiment, a plurality of conditions is stored in the measurement apparatus table 24 for each measurement apparatus 60. When one of the wearable devices 70 worn by the user who used the measurement apparatus 60 is not identified by a single condition stored in the measurement apparatus table 24, the association unit 16 may use another condition. The sequential use of a plurality of conditions as described above may increase the probability of successfully automatically associating the user with the measurement result.

Note that in the first embodiment, when the location information acquisition unit 12 may identify a single wearable device 70 whose location information satisfies a predetermined condition, the user wearing the wearable device 70 and the measurement apparatus 60 are automatically associated with each other. However, the embodiment is not limited thereto, and the embodiment may be configured such that, after values of each sensor (for example, an acceleration sensor) included in the sensors 189 are acquired and when only a single wearable device 70 has the acquired value satisfying a predetermined condition, the user wearing the single wearable device 70 is automatically associated with the measurement apparatus 60.

For example, when the measurement apparatus 60 is a body fat meter, the location information acquisition unit 12 may acquire the value of the acceleration sensor or the like. In this case, the condition may be whether or not the value of the acceleration sensor or the like indicates that the user keeps both arms extended in front for a predetermined time period. Note that, to determine whether or not such a condition is satisfied, the user has only to wear the acceleration sensor or the like on both arms. When the measurement apparatus 60 is a sphygmomanometer, the location information acquisition unit 12 may acquire the value of the acceleration sensor or the like. In this case, the condition may be whether or not the value of the acceleration sensor or the like indicates that the user keeps one arm extended in front for a predetermined time period. Note that the association unit 16 may identify the user who used the measurement apparatus 60 in accordance with whether or not both the value of the acceleration sensor or the like and the location information described above in the first embodiment satisfy a predetermined condition.

Note that although the case where the user uses the measurement apparatus 60 and the measurement result and the user are associated with each other when the measurement result is transmitted from the measurement apparatus 60 to the server 10 has been described in the first embodiment described above, the embodiment is not limited thereto. For example, a measurement result and a user may be associated with each other when the measurement result indicates an abnormal value exceeding a predetermined threshold and the user has to be informed thereof.

Second Embodiment

Next, a second embodiment will be described in detail in accordance with FIG. 8 to FIG. 13. The second embodiment is featured in that, even when the user and the wearable device 70 are not associated with each other, load on the user in associating the user with the wearable device 70 is reduced.

More specifically, in the second embodiment, when a wearable device worn by a user who used the measurement apparatus 60 is identified by the same method as in the first embodiment described above, a user is automatically associated with a measurement result by causing the user using the identified wearable device to enter user information by using an IC card or the like.

Figure 8:
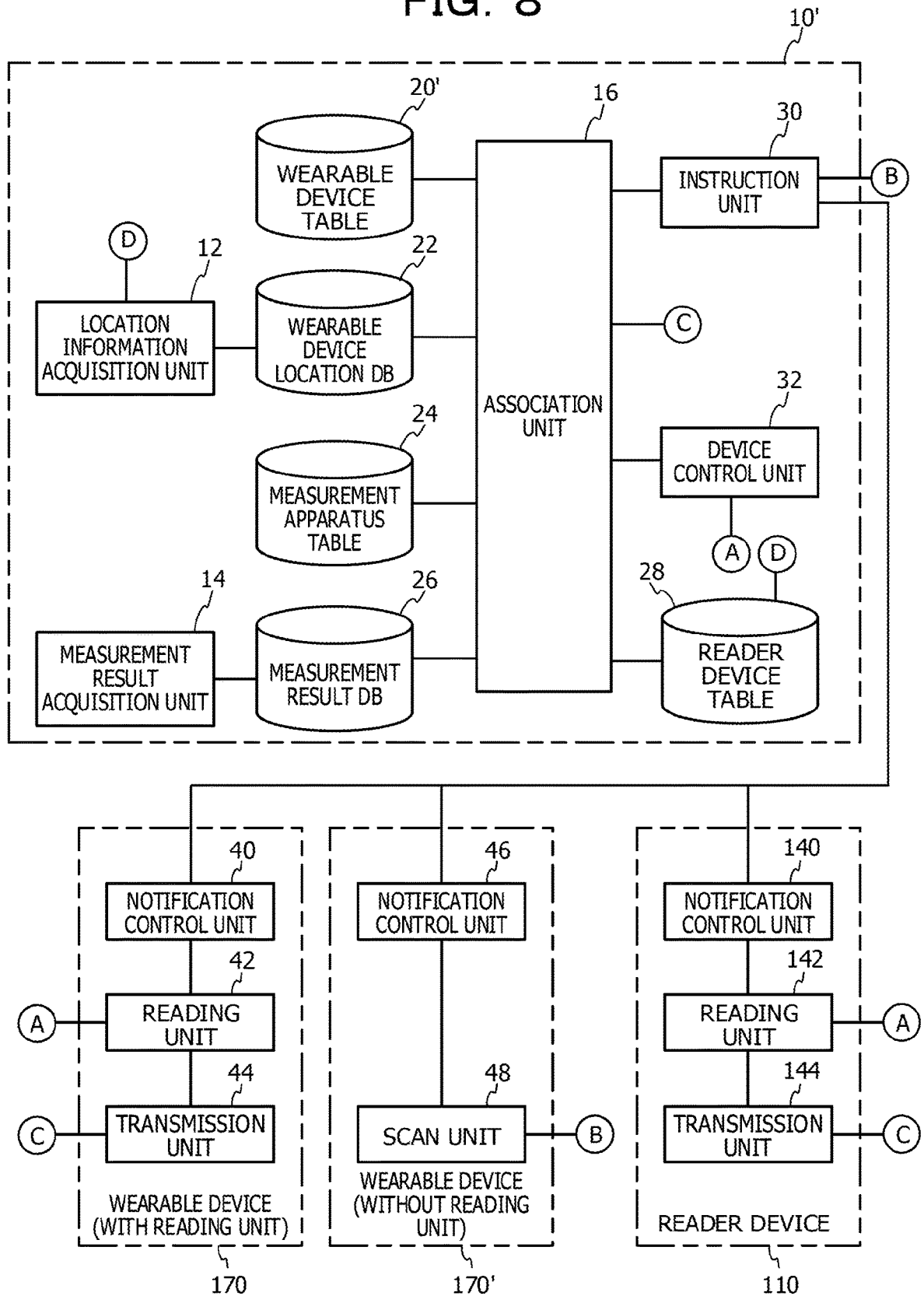
FIG. 8 is a function block diagram of a server according to a second embodiment.

FIG. 8 illustrates a function block diagram of a server 10' according to the second embodiment and a function block diagram of wearable devices 170 and 170' and a reader device 110. In the second embodiment, the wearable device 170 that has a reading unit 42 capable of reading user information from an IC card or the like carried by a user and the wearable device 170' that has no reading unit are present as a wearable device worn by the user. The reader device 110 is a smartphone or a PC and is a device having a reading unit 142.

As illustrated in FIG. 8, the wearable device 170 includes a notification control unit 40, the reading unit 42, and a transmission unit 44. The notification control unit 40 controls the display unit 193 (for example, an LED lamp) in accordance with an instruction from the server 10' and notifies the user of the time of reading user information. The reading unit 42 reads user information from an IC card or the like. Note that the reading unit 42 may not be a unit that reads user information from an IC card or the like but may be a unit that acquires user information (user ID or the like) manually input by the user or may be a unit that acquires a face image or a fingerprint image of the user as user information, for example. The reading unit 42 usually does not perform a reading process of user information but performs the reading process under the control of the device control unit 32 of the server 10'. The transmission unit 44 transmits user information read by the reading unit 42 to the association unit 16 of the server 10'.

The wearable device 170' includes a notification control unit 46 and a scan unit 48. The notification control unit 46 controls the display unit 193 (for example, an LED lamp) in accordance with an instruction from the server 10' and notifies the user of the time of reading user information. The scan unit 48 transmits an electromagnetic wave via the communication unit 197 in accordance with an instruction from the server 10', receives a response electromagnetic wave from the reader device 110 that receives the electromagnetic wave, and thereby scans the reader device 110 present nearby. The scan unit 48 transmits, to the server 10', the information on the reader device 110 detected by the scan.

The reader device 110 includes a communication control unit 140, the reading unit 142, and a transmission unit 144. The notification control unit 140, the reading unit 142, and the transmission unit 144 have the same functions as the notification control unit 40, the reading unit 42, and the transmission unit 44 of the wearable device 170, respectively.

As illustrated in FIG. 8, the server 10' includes an instruction unit 30 as a control unit, a device control unit 32, and a reader device table 28 in addition to the same function, DB, and table as those in the first embodiment described above. Further, the server 10' includes a wearable device table 20' instead of the wearable device table 20.

The wearable device table 20' has the table structure as illustrated in FIG. 9A. The wearable device table 20' has items of "reading unit" and "notification" in addition to items of "device ID" and "user" as may be seen from comparison to the wearable device table 20 of the first embodiment (FIG. 4A). The wearable device table 20' stores therein information on a user associated with a device ID ("–" when no associated user is present), the presence or absence of a reading unit, and information on a notification unit when notifying a user (an LED lamp, a display, a sound, or the like).

When instructing the user to cause user information to be read, the instruction unit 30 outputs a notification instruction to the notification control unit (40 or 46) of the wearable device (170 or 170') worn by the user. Further, when the wearable device is the wearable device 170' having no reading unit, the instruction unit 30 outputs a scan instruction to the scan unit 48 of the wearable device 170'. In response to receiving information on the detected reader device 110 from the wearable device 170' as a result of scan, the instruction unit 30 refers to the reader device table 28 to identify the reader device 110 that is closest to the wearable device 170' out of the identified reader devices 110 and outputs a notification instruction to the notification control unit 140 of the identified reader devices 110. Note that, for example, when each notification unit is an LED lamp, the notification control unit 46 of the wearable device 170' and the notification control unit 140 of the reader device 110 cause LED lamps to blink at the same interval at the same time so as to have synchronous blinking in accordance with a notification instruction from the instruction unit 30. When the notification unit is a display, the notification control unit 140 displays "User who used A001 for measurement, please cause reader device to read user information in the direction indicated by arrow". When the notification unit uses a sound, the notification control unit 140 causes the wearable device and the reader device to output the same sound or output a sound at the same time. That is, when the notification unit uses a sound, the notification control unit 140 causes a sound output unit of the wearable device to output a sound and causes a sound output unit of the reader device to output a sound corresponding to the sound of the wearable device.

As illustrated in FIG. 10B, information on a unit (an LED lamp, a display, or the like) when the reader device 110 notifies the user (see the "notification" field) and "location information" of the reader device 110 are stored in the reader device table 28 on a "reader device ID" basis. Since the location information acquisition unit 12 acquires the location information on the reader device 110 all the time in addition to the location information on the wearable devices 170 and 170', the latest location information on the reader device 110 is stored in the "location information" field in the reader device table 28.

The device control unit 32 controls the reading unit 142 so as to enable reading of an IC card or the like in the reader device 110 during a predetermined time period after synchronous blinking is started.

Note that the wearable device location DB 22, the measurement apparatus table 24, and the measurement result DB 26 are the same as those in the first embodiment as illustrated in FIG. 9B, FIG. 9C, and FIG. 10A.

(Process in Server 10')

Next, the process in the server 10' according to the second embodiment will be described in detail in accordance with flowcharts in FIG. 12 and FIG. 13 and with reference to other drawings.

Figure 11:
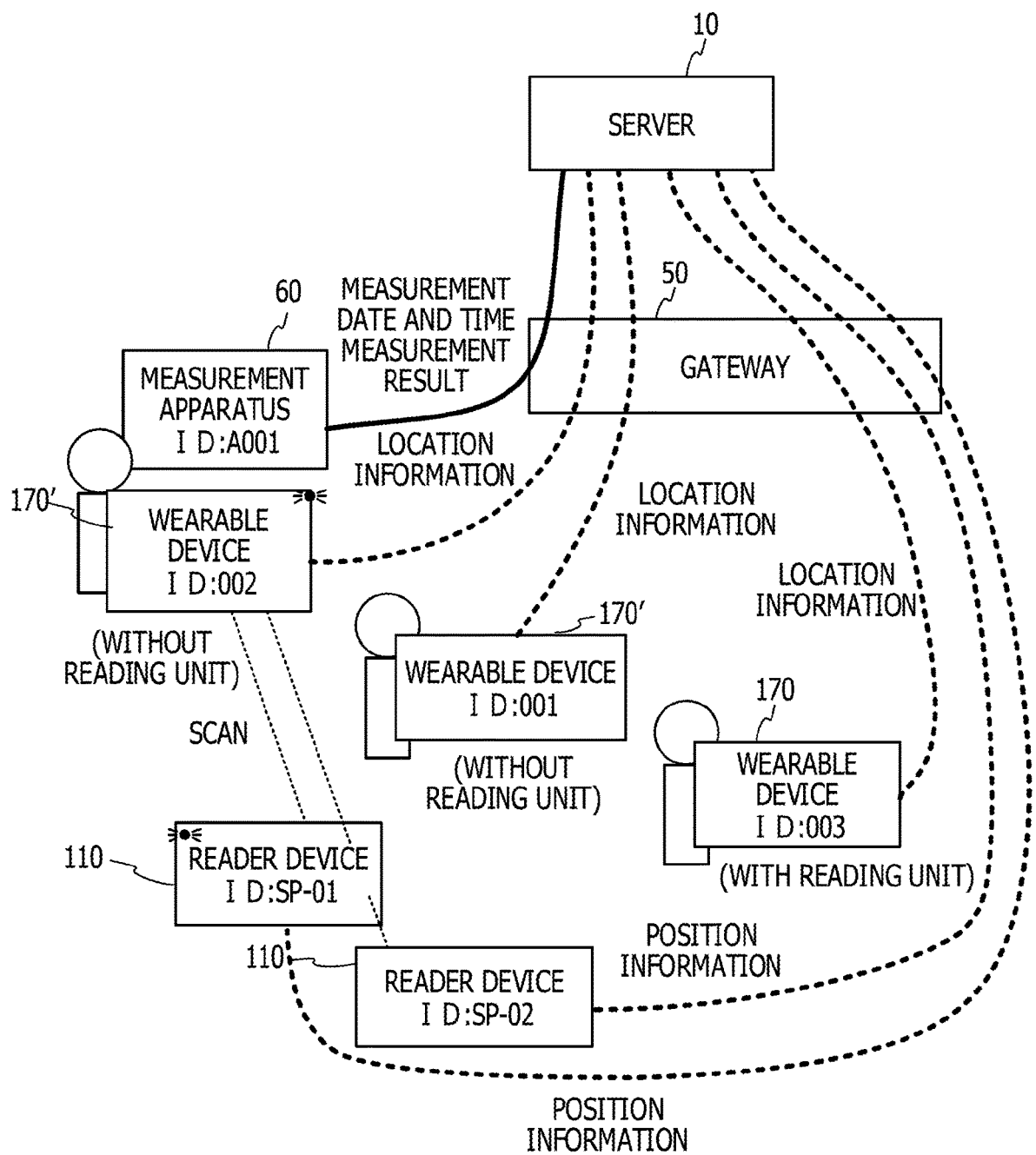
FIG. 11 is a diagram illustrating transaction of data in the second embodiment.
Figure 12:
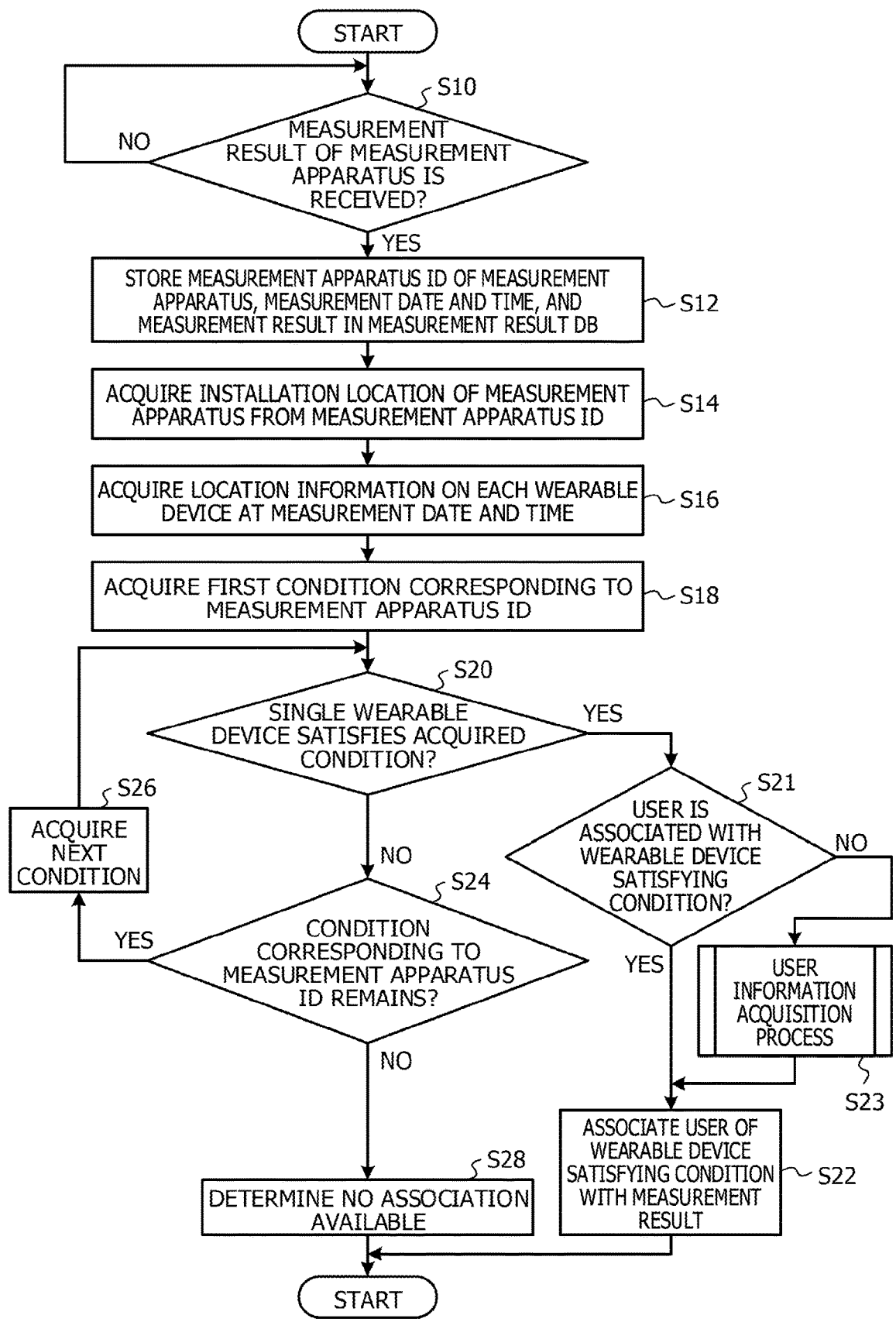
FIG. 12 is a flowchart illustrating a process in the server according to the second embodiment.
Figure 13:
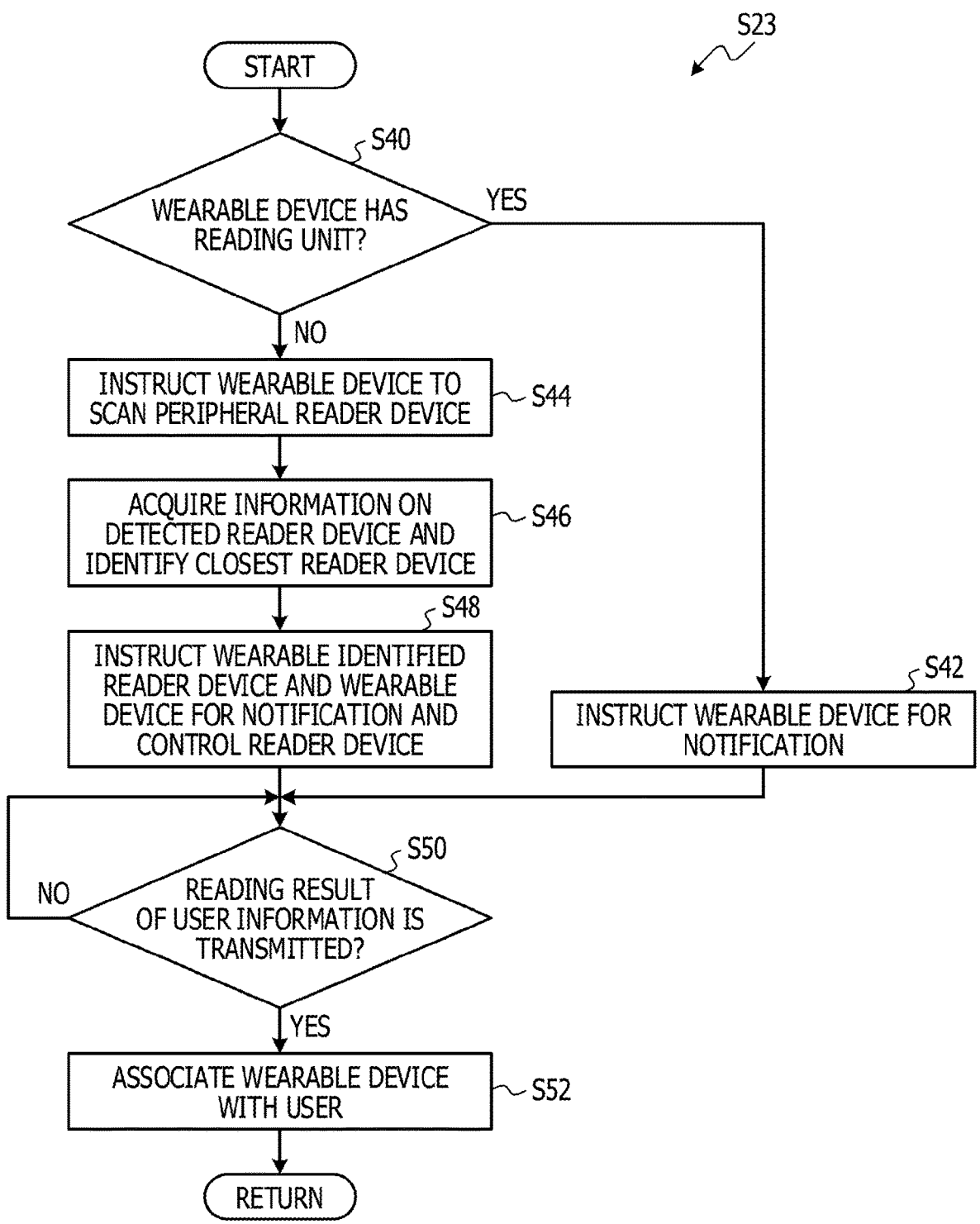
FIG. 13 is a flowchart illustrating a specific process of step S23 in FIG. 12.

Note that, before the process in FIG. 12 and FIG. 13, the user using the measurement apparatus 60 (ID=A001) (the user wearing the wearable device 170' (ID=002) having no reading unit) is assumed to be present near the measurement apparatus 60, as illustrated in FIG. 11. Further, there are a user wearing the wearable device 170' (ID=001) located somehow distant from the measurement apparatus 60 and a user wearing the wearable device 170 (ID=003) having the reading unit 42. Further, the reader device 110 (ID=SP-01, SP-02) is present near the measurement apparatus 60.

Further, before the process in FIG. 11, information on each of the wearable devices 170 and 170' is stored in the wearable device table 20', and information on each measurement apparatus 60 is stored in the measurement apparatus table 24. Further, information on the reader device 110 is stored in the reader device table 28. Further, location information is transmitted from the wearable devices 170 and 170' and the reader device 110, and the location information acquisition unit 12 updates the "location" field of the wearable device location DB 22 or the reader device table 28 with the received location information (see the bold dashed line in FIG. 11).

Once the process in FIG. 11 is started, the operations of steps S10 to S20 and S24 to S28 are performed in the same manner as in the first embodiment described above. That is, upon receiving a measurement result of the measurement apparatus 60 (S10: Yes, see the bold solid line in FIG. 11), the measurement result acquisition unit 14 stores the measurement result in the measurement result DB 26 (S12), and the association unit 16 determines whether or not one of the wearable devices 170 and 170' whose location at the measurement date and time of the measurement apparatus 60 satisfies the condition (see condition 1, condition 2 in FIG. 9C) is identified (S14 to S20, S24, and S26). Then, when no wearable device is identified by using any of the conditions, the association unit 16 determines that no association is available between the user and the measurement result (S28).

On the other hand, if one of the wearable devices 170 and 170' whose location at the measurement date and time of the measurement apparatus 60 satisfies the condition is identified, the association unit 16 proceeds to step S21.

Upon proceeding to step S21, the association unit 16 determines whether or not the user has already associated with the wearable device 170 or 170' which satisfies the condition. That is, the association unit 16 refers to the wearable device table 20' and sees whether or not the user has already associated with the device ID of the wearable device 170 or 170' which satisfies the condition. If the determination in step S21 is YES, the process proceeds to step S22 to associate the user with the measurement result in the same manner as in the first embodiment described above.

On the other hand, if the determination in step S21 is NO, the process proceeds to step S23. In step S23, the process in accordance with the flowchart in FIG. 13 is performed.

In the process in FIG. 13, first, in step S40, the association unit 16 determines whether or not the wearable device satisfying the condition has a reading unit, that is, whether or not the wearable device satisfying the condition is the wearable device 170. Note that the association unit 16 refers to the "reading unit" field of the wearable device table 20' in the determination in step S40. If the determination in step S40 is YES, the process proceeds to step S42. In step S42, the instruction unit 30 instructs the wearable device 170 to notify the user that a reading process of user information starts. In this case, the instruction unit 30 refers to the "notification" field in the wearable device table 20 and instructs the notification control unit 40 of the wearable device 170 to perform notification using a unit (for example, an LED lamp, a display, or the like) described in the "notification" field. In the wearable device 170, the notification control unit 40 controls notification (for example, blinking of the LED lamp). This enables user to be notified that it is the time of reading of user information on the wearable device 170.

After step S42, the association unit 16 proceeds to step S50 and stands by until the reading result of user information is transmitted from the wearable device 170. In this case, when the user places an IC card in front of the reading unit 42 to cause the reading unit 42 to read user information, the user information is transmitted from the transmission unit 44 to the association unit 16. Thereby, the process proceeds to step S52. In step S52, the association unit 16 registers, to the wearable device table 20, information on the user wearing the wearable device 170 satisfying the condition and thereby associates the wearable device 170 with the user. The association unit 16 then proceeds to step S22 in FIG. 12 and performs the process of associating the user with the measurement result. Then, the entire process in FIG. 12 ends.

On the other hand, if the determination in step S40 in FIG. 13 is NO, that is, if the wearable device satisfying the condition is the wearable device 170', the process proceeds to step S44. Note that it is assumed that the wearable device satisfying the condition is the wearable device 170' of the device ID=002 illustrated in FIG. 11.

Upon proceeding to step S44, the instruction unit 30 instructs the scan unit 48 of the wearable device 170' (ID=002) to scan the peripheral reader devices 110. In the wearable device 170', the scan unit 48 scans the peripheral reader devices 110, detects the reader devices 110 (for example, ID=SP-01, SP-02) present nearby, and transmits information on the detected reader devices 110 to the instruction unit 30.

Next, in step S46, the instruction unit 30 acquires information on the detected reader device 110 and refers to the "location" field in the reader device table 28 (FIG. 10B) to identify the reader device 110 that is the closest to the wearable device 170'. As an example, it is assumed that the reader device 110 having ID=SP-01 is identified.

Next, in step S48, the instruction unit 30 instructs the identified reader device 110 (ID=SP-01) and the wearable device 170' (ID=002) to perform notification and controls reading performed by the reading unit 142 of the reader device 110 (ID=SP-01). In this case, for example, the identified reader device 110 and the wearable device 170' are controlled to cause LED lamps thereof to synchronously blink, and thereby the user is able to determine which reader device 110 to use for reading of an IC card or the like. Further, the reading unit 142 of the reader device 110 controls the time of reading to restrict the time during which reading is performed by the reading unit 142, and this allows a reduced likelihood of another user performing reading of an IC card or the like. Note that the blinking interval may be differed in accordance with the distance between the reader device 110 and the wearable device 170, for example. For example, the blinking interval may be shorter for a shorter distance between the reader device 110 and the wearable device 170. This enables the user to intuitively recognize approaching to the reader device 110.

After step S48, the association unit 16 stands by until a reading result of user information is transmitted (S50) and, upon the transmission of the reading result of user information, associates the wearable device 170' with the user in the wearable device table 20' (S52). The association unit 16 then proceeds to step S22 in FIG. 12 and, after performing association of the user with the measurement result, completes the entire process in FIG. 12.

As described above in detail, according to the second embodiment, the location information acquisition unit 12 acquires location information from the wearable devices 170 and 170', and the measurement result acquisition unit 14 acquires a measurement result in the measurement apparatus 60. Further, the association unit 16 identifies the wearable device 170 or 170' whose location has satisfied a predetermined condition when measurement is performed by the measurement result acquisition unit 14. The instruction unit 30 then causes the identified wearable device 170 or 170' to display notification that prompts the user to input user information (reading of an IC card or the like). Thereby, it is possible to prompt the user who used the measurement apparatus 60 to input user information used for association with the measurement result. Therefore, when the user inputs user information by using the wearable device 170 worn by itself or the reader device 110 present nearby, this enables the association unit 16 to associate the user with the measurement result in a simple manner even when the user and the wearable device 170 or 170' have not been associated in advance.

Further, in the second embodiment, when an identified wearable device is the wearable device 170' having no reading unit, the instruction unit 30 causes the LED lamp of the wearable device 170' to blink and causes the LED lamp of the reader device 110 present in the nearest location to synchronously blink. This enables the user to easily determine which reader device 110 to use for reading of an IC card or the like.

Note that, in the second embodiment, the case where the scan unit 48 of the wearable device 170' scans the reader device 110 nearby and the instruction unit 30 identifies the reader device 110 which is the closest to the wearable device 170' in accordance with the "location" field in the reader device table 28 in steps S44 and S46 has been described. However, the embodiment is not limited thereto, and the scan unit 48 or the instruction unit 30 may identify the reader device 110 which is the closest to the wearable device 170' in accordance with a response radio wave intensity from the reader device 110 at the time of a scan performed by the scan unit 48, for example.

Note that, while the case where the user uses the measurement apparatus 60 and, when a measurement result is transmitted from the measurement apparatus 60 to the server 10, the user is instructed to input user information has been described above in the second embodiment, the embodiment is not limited thereto. For example, when the user wears the wearable device 170', the embodiment may be configured to instruct the user to input user information when the wearable device 170' comes close to any of the reader devices 110 within a predetermined distance.

Note that, while the case where information on the reader device 110 is stored in the reader device table 28 has been described above in the second embodiment, in addition thereto, information on the wearable device 170 having the reader device unit 42 may be stored.

Note that, while the case where the reader device 110 which is the closest to the wearable device 170' is identified in step S46 has been described above in the second embodiment, the embodiment is not limited thereto. For example, the reader device 110 nearby having the same notification unit as the wearable device 170' may be identified.

Note that, while the case where the LED lamps of the wearable device 170' and the reader device 110 area caused to synchronously blink and thereby the user is notified that the reader device 110 is capable of reading user information has been described above in the second embodiment, the embodiment is not limited thereto. That is, another notification scheme may be employed as long as it may notify the user that the reader device 110 is capable of reading user information.

Third Embodiment

Next, a third embodiment will be described in detail in accordance with FIG. 14 to FIG. 17. While having the same system configuration as that in FIG. 1 and performing the same process as that in the first embodiment described above, an information processing system of the third embodiment is featured in that, if the determination in step S24 in FIG. 6 is NO (when no wearable device is singled out), an inquiry process to the multiple candidate users of the wearable devices 70 is performed without the process of step S28 being performed.

Figure 14:
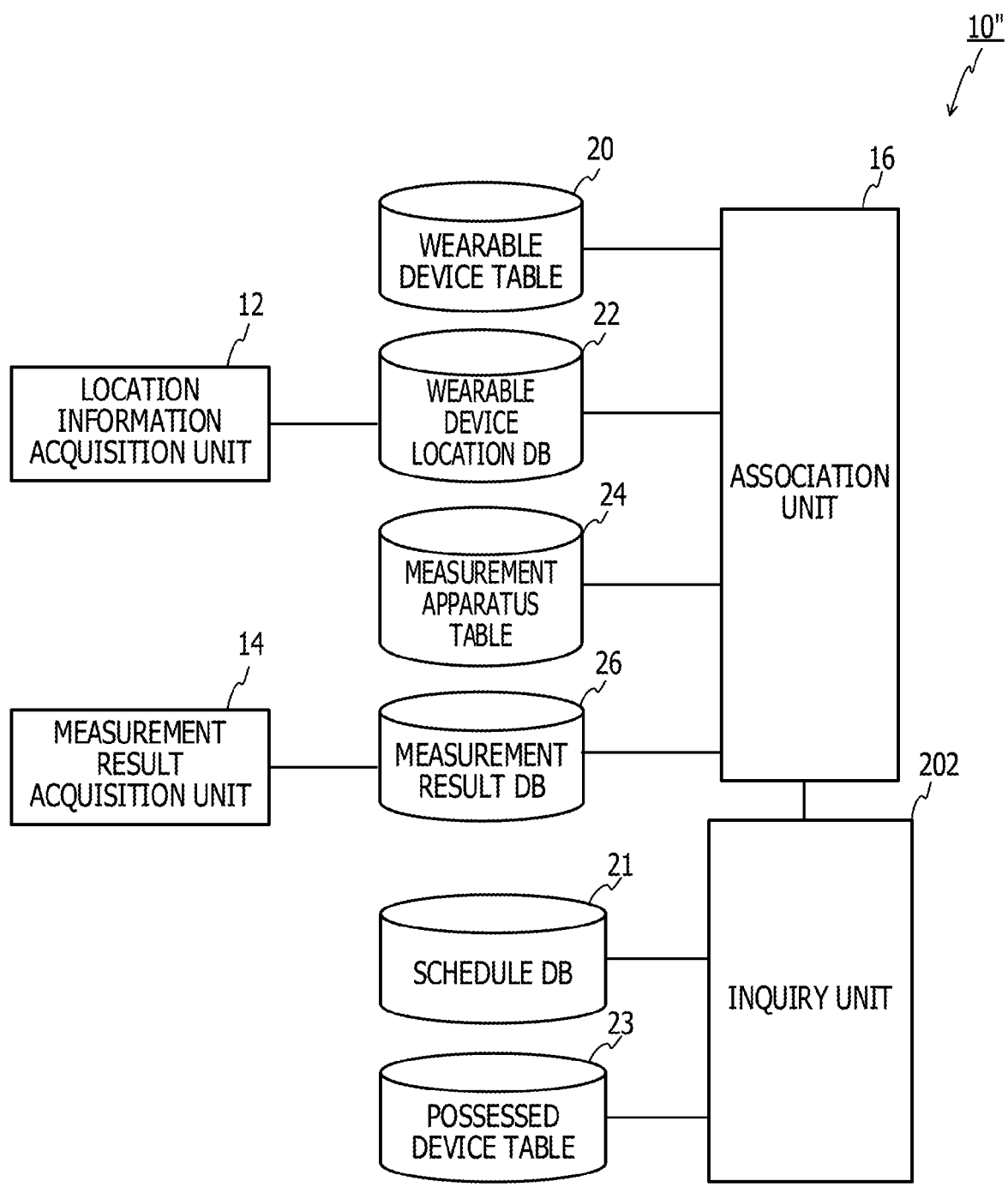
FIG. 14 is a function block diagram of a server according to a third embodiment.

FIG. 14 illustrates a function block diagram of a server 10" according to the third embodiment. As illustrated in FIG. 14, in the third embodiment, the server 10" includes an inquiry unit 202 in addition to the configuration of the server 10 in FIG. 3, and the inquiry unit 202 refers to a schedule DB 21 and a possessed device table 23 stored in the storage unit 96 or the like. Note that the inquiry unit 202 has a function of a transmission unit that transmits inquiry information to the multiple users of the wearable devices 70 when the association unit 16 was unable to identify a single wearable device 70.

The schedule DB 21 is a database that manages schedules of respective users and has the data structure as illustrated in FIG. 15A. That is, the schedule DB 21 stores "contents", start date and time, and end date and time ("date", "start", and "end") of schedules on a "user" basis.

The possessed device table 23 is a table that manages information on devices processed by users and has the table structure as illustrated in FIG. 15B. That is, the possessed device table 23 stores information on "possessed device" possessed by users and information on the current "state" of the device (a login state, a power-off state, or the like) on a "user" basis. Note that the "state" field is updated by the inquiry unit 202 in accordance with information obtained through communication between the server 10" and respective devices.

(Process in Server 10")

The process in the server 10" will be described below in accordance with FIG. 16 and FIG. 17.

Figure 16:
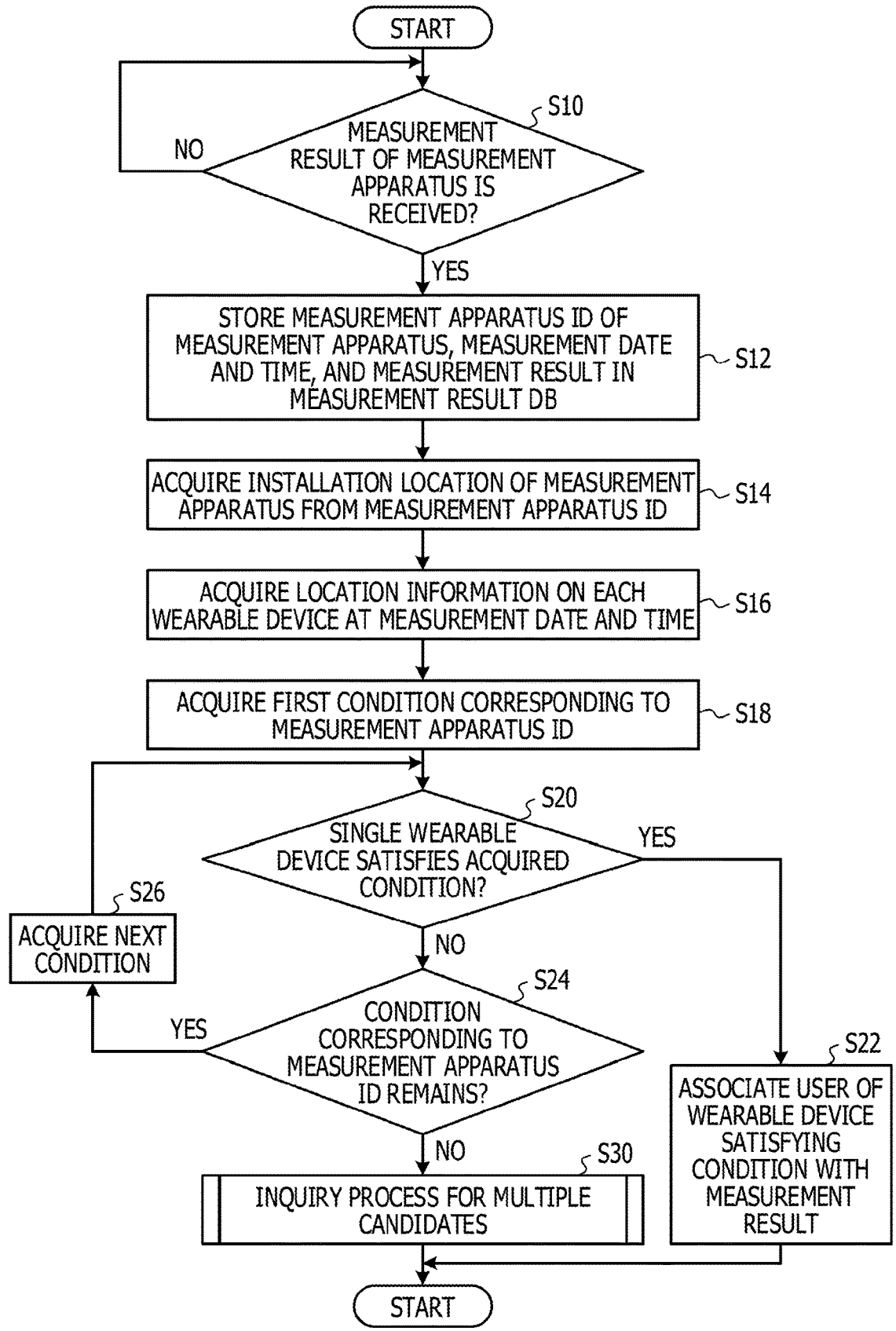
FIG. 16 is a flowchart illustrating a process in the server according to the third embodiment.

FIG. 16 is a flowchart illustrating the process of the server 10" according to the third embodiment. As illustrated in FIG. 16, the server 10" performs the process in the same manner as in the first embodiment (FIG. 6) up to step S26, however, if the determination in step S24 is NO, performs the process of step S30. Note that the case of proceeding to step S30 means a case where the wearable device 70 of the user who used the measurement apparatus 60 is not singled out and there are multiple candidates of the wearable devices 70.

In step S30, an inquiry process to multiple candidates. Specifically, the process of step S30 is performed in accordance with the flowchart in FIG. 17.

Figure 17:
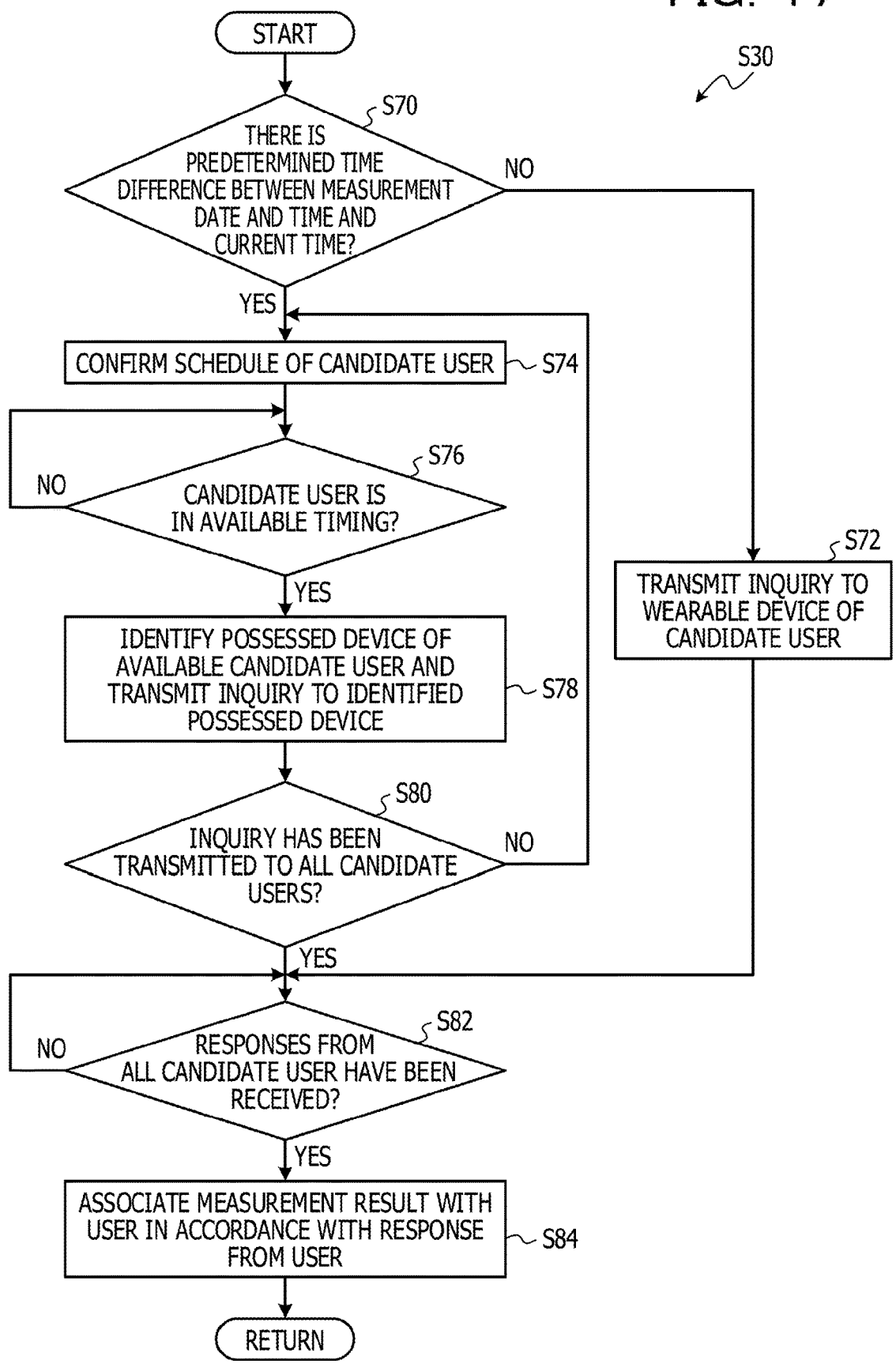
FIG. 17 is a flowchart illustrating a specific process of step S30 in FIG. 16.

In the process in FIG. 17, first, in step S70, the inquiry unit 202 determines whether or not there is a predetermined time difference between the measurement date and time and the current time. Note that the case where the determination in step S70 is NO means a case where time is taken before a measurement result is transmitted from the measurement apparatus 60 to the server 10".

If the determination in step S70 is NO, the process proceeds to step S72. In this case, since each candidate user is likely to be located near the measurement apparatus 60, the inquiry unit 202 transmits an inquiry to the wearable device 70 of each user. In this case, a message such as "Did you use measurement apparatus just now?" is displayed on the display unit 193 of the wearable device 70. In response, the candidate user may select and respond with a response "Yes" or "No".

On the other hand, if the determination in step S70 is YES, the process proceeds to step S74, and the inquiry unit 202 refers to the schedule DB 21 and confirms the schedule of the candidate user.

Next, in step S76, the inquiry unit 202 stands by until any of the candidate users is in an available time. The available time means a time zone in which no schedule has been set, for example. Once any of the candidate users is in an available time, the inquiry unit 202 proceeds to step S78.

When the process proceeds to step S78, the inquiry unit 202 refers to the possessed device table 23, identifies a possessed device of each available candidate user, and transmits an inquiry to the possessed device. In this case, in the same manner as in the case of step S72, a message such as "Did you use measurement apparatus just now?" is displayed on the display unit 193 of the wearable device 70. In response, the candidate user may select and respond with a response "Yes" or "No".

Next, in step S80, the inquiry unit 202 determines whether or not the inquiry has been transmitted to all the candidate users. If the determination in step S80 is NO, the process returns to step S74, and if the determination in step S80 is YES, the process proceeds to step S82.

When the process proceeds to step S82, the inquiry unit 202 stands by until receiving responses of all the candidate users. When responses from all the candidate users are received, the process proceeds to step S84, and the association unit 16 associates the measurement result of the measurement apparatus 60 with the user in accordance with the responses from the users. Note that, when there are multiple users who respond with "Yes", the association unit 16 is unable to identify a single user and thus may determine that no association is available as with step S28 in the first embodiment.

As described above, according to the third embodiment, when candidate users are inquired for usage of the measurement apparatus 60, the inquiry is performed taking schedules of the candidate users into consideration when a predetermined time has elapsed from the usage of the measurement apparatus 60. Thereby, it is possible to perform inquiry so as not to bother candidate users.

Further, when the candidate users are inquired as described above, a user who used the measurement apparatus 60 may be singled out even when there are multiple candidate users.

Note that, in the third embodiment described above, when the inquiry unit 202 identifies a possessed device from the processed device table 23, the possessed device may be identified taking the location of the user' (wearable device) into consideration. For example, when the user is in an office, a PC is identified as a possessed device, and when the user is out, a smartphone is identified as a possessed device.

Modified Examples

Note that, while the case where information on the measurement apparatus 60, the wearable device 70, 170, or 170', or the reader device 110 is managed in various tables of the server 10, 10', or 10" has been described in each of the above embodiments, the embodiment is not limited thereto. For example, a profile of each apparatus or each device may be exposed and thereby information demanded for a server may be acquired.

Note that, while the case where a wearable device uses a GPS sensor to acquire location information has been described in the above embodiments, the embodiment is not limited thereto. For example, a wearable device in configured to receive an ID and a signal intensity (RSSI) of a plurality of positioning beacons arranged in a movable range of the wearable device and acquire the beacon location in accordance with the ID of the received beacon from a beacon map (table storing locations of respective beacons) created in advance. The wearable device may then estimate the current location by performing weighting in accordance with the signal intensity on a beacon location basis to obtain a weighting average.

Figure 18:
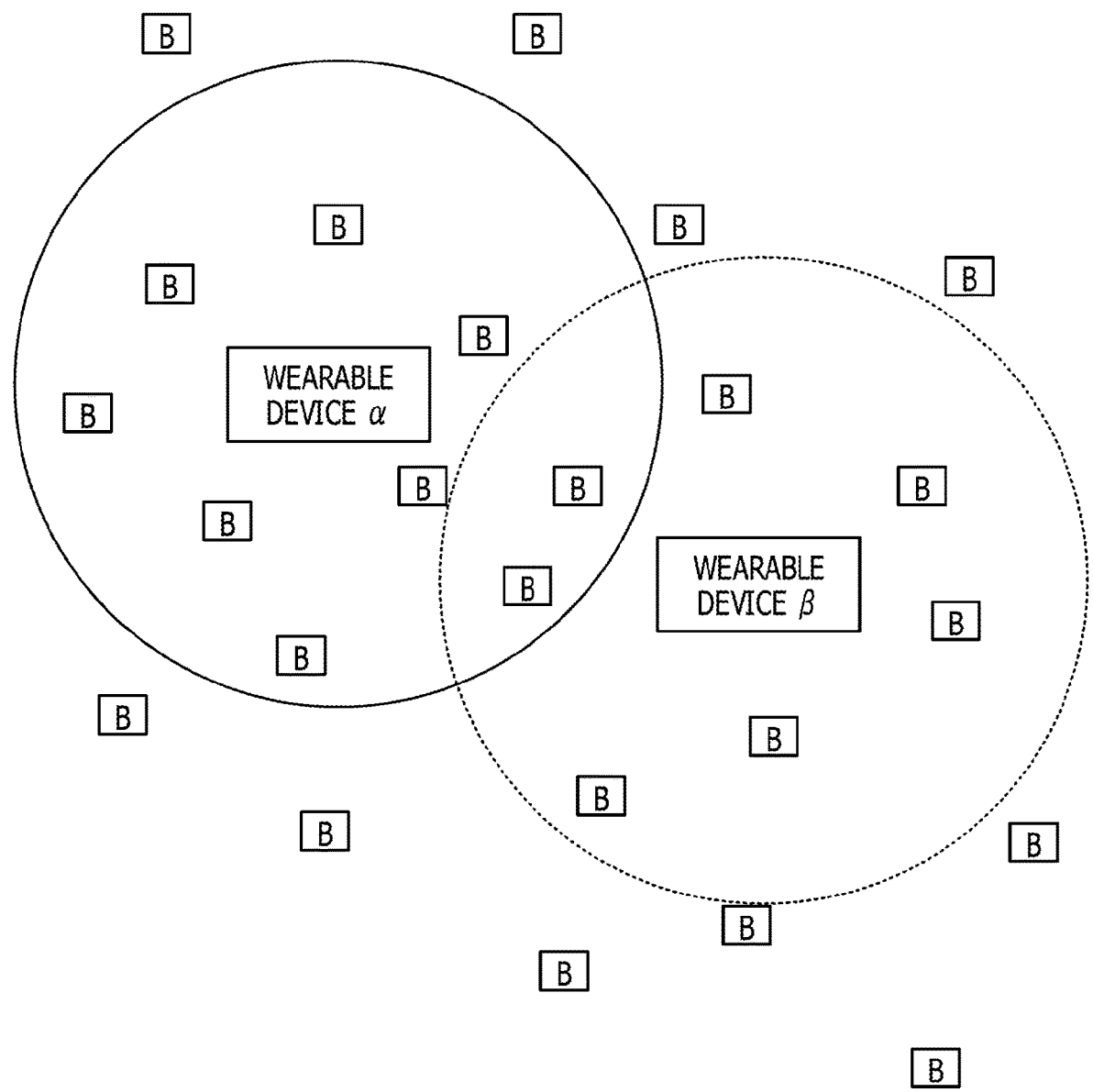
FIG. 18 is a diagram illustrating a method of distributing a beacon map according to a modified example.

Note that, when the beacon map described above is used, to address a limited capacity for storing beacon information in the wearable device, a beacon map may be transmitted from a server or the like to the wearable device to rewrite the beacon map stored in the wearable device. In this case, the server or the like may transmit a beacon map near the wearable device in accordance with the location of the wearable device. For example, the server or the like may transmit, to the wearable device α in FIG. 18, a beacon map including information on beacons present within a range surrounded by the solid-line circle (denoted as symbol "B") and transmit, to the wearable device β in FIG. 18, a beacon map including information on beacons present within a range surrounded by the dashed-line circle. This enables accurate estimation of the location of the wearable device even with a small storage capacity of the wearable device.

Figure 20A:
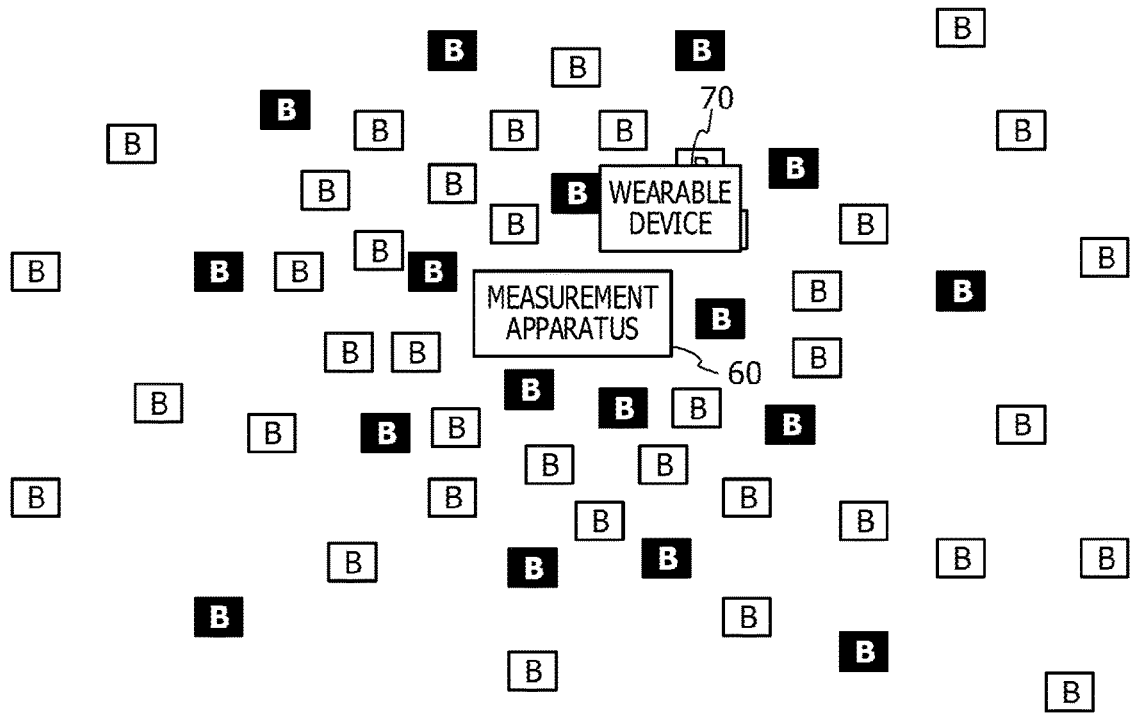
FIG. 20A and FIG. 20B are diagrams illustrating a method of distributing a beacon map in the example in FIG. 19.
Figure 20B:
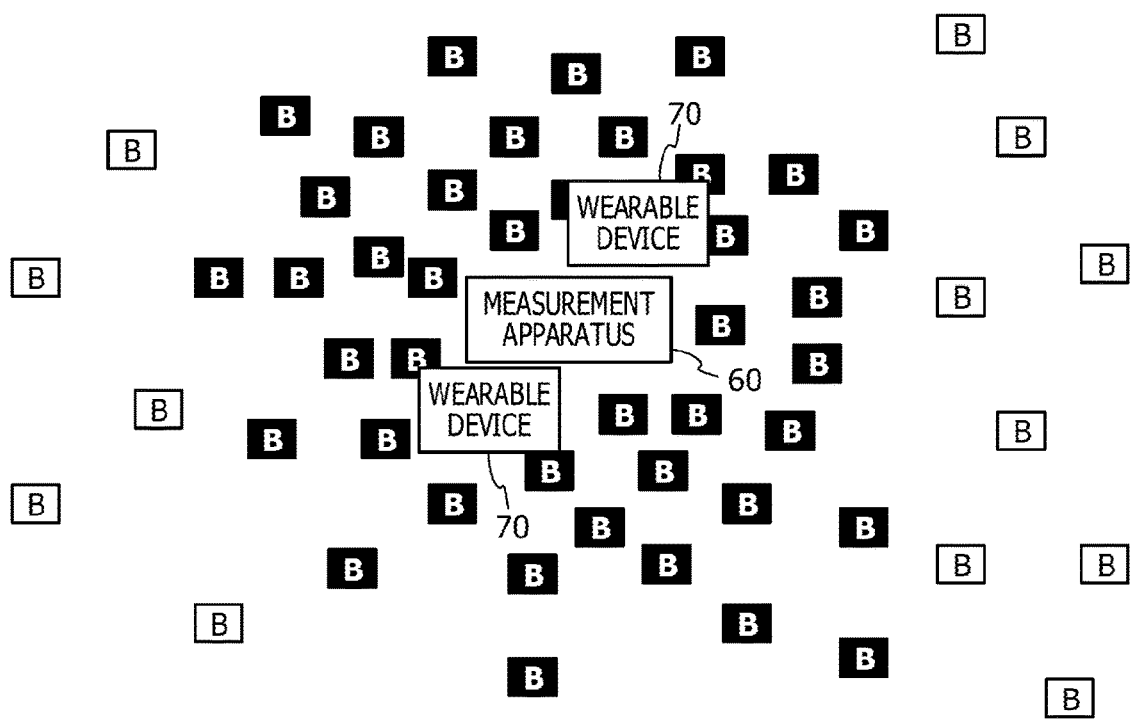

Further, as illustrated in FIG. 19, beacons may be densely arranged near the measurement apparatus 60. In this case, as illustrated in FIG. 20A, when a single wearable device 70 (170, 170') is present near the measurement apparatus 60, the server or the like transmits, to the wearable device of interest, a beacon map from which some of the densely arranged beacons are reduced (a map including information on the beacons indicated in black in FIG. 20A). Further, as illustrated in FIG. 20B, when a plurality of wearable devices are present near the measurement apparatus 60, a beacon map from which none of the densely arranged beacons is reduced (a map including information on the beacons indicated in black in FIG. 20B). This enables accurate estimation of the location of the wearable device even when a plurality of wearable devices is present near the measurement apparatus 60.

Figure 21:
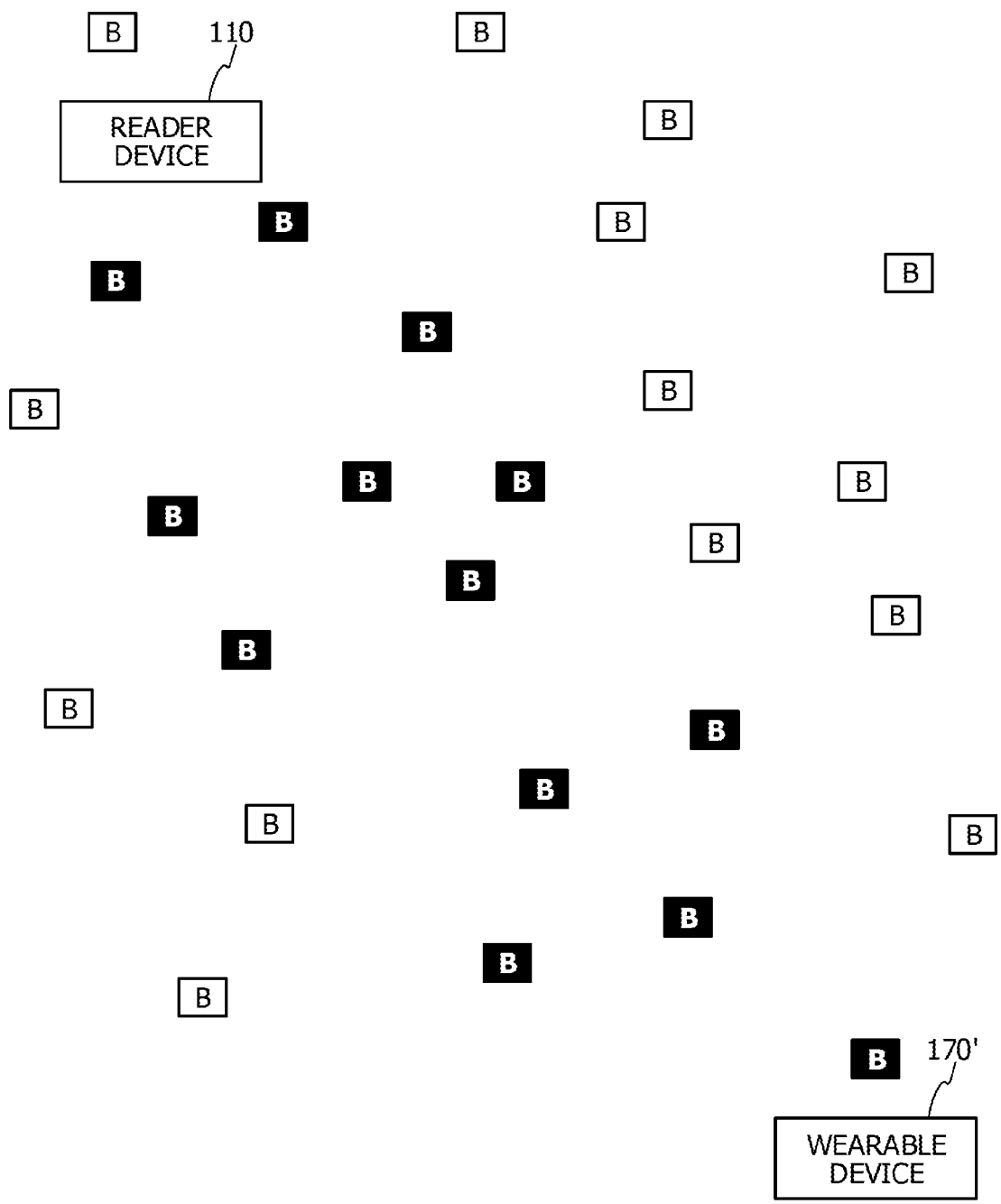
FIG. 21 is a diagram illustrating a method of distributing a beacon map when guiding a user to a reader device in the modified example.

Note that, in the second embodiment described above, when the beacon map as described above is used, the server may distribute, to the wearable device 170', information on beacons which are present between the wearable device 170' and the reader device 110 (beacon information indicated in black in FIG. 21) as a beacon map, as illustrated in FIG. 21. In this case, when a user wearing the wearable device 170' moves in a correct direction, a large amount of beacon information included in the beacon map is received, and when the user moves in a wrong direction, substantially no beacon information included in the beacon map is received. Therefore, since it is possible to determine whether or not the direction in which the user moves is the correct direction in accordance with the number of pieces of received beacon information included in a beacon map, it is possible to correctly guide the user to a reader device by notifying the use of the determination result in the wearable device (turning on a green lamp if the direction is correct, and turning on a red lamp if the direction is wrong).

Note that, in each of the embodiments described above, the gateway 50 may be omitted when the measurement apparatus 60, the wearable devices 70, 170, or 170', or the reader device 110 may be directly connected to the network 80.

Note that the processing functions described above may be implemented by a computer. In this case, a program including a plurality of program instructions describing the process contents of the function to be included in a processing apparatus is provided. When the plurality of program instructions is executed by the computer, the processing functions described above are implemented on the computer. The program including the plurality of program instructions describing the process contents may be stored in a computer readable storage medium (except a carrier wave).

When the program is distributed, such a program may be sold in a form of a portable storage medium such as a digital versatile disc (DVD), a compact disc read-only memory (CD-ROM), or the like, for example. Further, the program may be stored in a storage device of a computer in advance and then transferred from a server computer to another computer via a network.

A computer executing the program stores, in a storage device thereof, a program stored in a portable storage medium or a program transferred from a server computer, for example. The computer then reads the program from the storage device thereof and performs the process in accordance with the program. Note that the computer may directly read a program from a portable storage medium and perform the process in accordance with the program. Further, the computer may perform the program in accordance with received programs sequentially every time the program is transferred from the server computer.

The embodiments described above are examples of preferred implementations. Without being limited thereto, however, various modifications are possible within the scope not departing from the spirit of the embodiment.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A measurement result management apparatus comprising:
   one or more memories; and
   one or more processors coupled to the one or more memories and the one or more processors configured to
      acquire, from a plurality of devices worn by a plurality of users, location information indicating locations of the plurality of devices,
      perform, in response to acquisition of a first measurement result including a first measurement time from a first measurement apparatus which measures a condition of a user wearing a device, a selection of a first device from the plurality of devices by comparing locations of the plurality of devices at the first measurement time with a location of the first measurement apparatus, and
      store the condition of a user measured by the first measurement apparatus in association with user identification information of the selected first device in the one or more memories.

2. The measurement result management apparatus according to claim 1, wherein the selection includes selecting, from the plurality of devices, the first device in a location satisfying a first condition associated with the first measurement apparatus.

3. The measurement result management apparatus according to claim 1, wherein
   the one or more memories store a first condition and a second condition associated with the first measurement apparatus, and
   the selection includes selecting, from the plurality of devices, the first device in a location satisfying the second condition when it is determined that no device in a location satisfying the first condition is included in the plurality of devices.

4. The measurement result management apparatus according to claim 1, wherein the one or more processors configured to perform, when a first plurality of devices are selected from the plurality of devices in accordance with a location of a second measurement apparatus, a second measurement time, and the location information in response to acquisition of a second measurement result including the second measurement time from the second measurement apparatus, transmission of inquiry information to each of the first plurality of devices.

5. The measurement result management apparatus according to claim 4, wherein the transmission includes determining a transmission time of the inquiry information in accordance with a schedule associated with each of the first plurality of devices.

6. The measurement result management apparatus according to claim 4, wherein the transmission includes determining a transmission time of the inquiry information in accordance with a location of each of the plurality of devices.

7. The measurement result management apparatus according to claim 1, wherein the one or more processors configured to transmit, to the first device, information that instructs a user to input user information.

8. The measurement result management apparatus according to claim 1, wherein the one or more processors configured to store, in the memory in association with the first measurement result, information inputted by a user in response to outputting information that instructs the user to input user information.

9. The measurement result management apparatus according to claim 1,
   wherein the one or more processors configured to transmit, to an input device associated with the first device, information that instructs a user to input user information, and
   wherein the input device configured to output at least one of a light and a sound from an output apparatus of the input device in response to receiving the information.

10. A computer-implemented measurement result management method comprising:
    acquiring, from a plurality of devices worn by a plurality of users, location information indicating locations of the plurality of devices;
    selecting, in response to acquisition of a first measurement result including a first measurement time from a first measurement apparatus which measures a condition of a user wearing a device, a first device from the plurality of devices by comparing locations of the plurality of devices at the first measurement time with a location of the first measurement apparatus; and
    storing the condition of a user measured by the first measurement apparatus in association with user identification information of the selected first device in a memory.

11. The measurement result management method according to claim 10, wherein the selecting includes selecting, from the plurality of devices, the first device in a location satisfying a first condition associated with the first measurement apparatus.

12. The measurement result management method according to claim 10, wherein the memory stores a first condition and a second condition associated with the first measurement apparatus, and the selecting includes selecting, from the plurality of devices, the first device in a location satisfying the second condition when it is determined that no device in a location satisfying the first condition is included in the plurality of devices.

13. The measurement result management method according to claim 10, further comprising: when a first plurality of devices are selected from the plurality of devices in accordance with a location of a second measurement apparatus, a second measurement time, and the location information in response to acquisition of a second measurement result including the second measurement time from the second measurement apparatus, transmitting of inquiry information to each of the first plurality of devices.

14. The measurement result management method according to claim 13 wherein the transmitting includes determining a transmission time of the inquiry information in accordance with a schedule associated with each of the first plurality of devices.

15. The measurement result management method according to claim 13, wherein the transmission includes determining a transmission time of the inquiry information in accordance with a location of each of the plurality of devices.

16. The measurement result management method according to claim 10, further comprising: transmitting, to the first device, information that instructs a user to input user information.

17. The measurement result management method according to claim 10, further comprising: storing, in the memory in association with the first measurement result, information inputted by a user in response to outputting information that instructs the user to input user information.

18. The measurement result management method according to claim 10, further comprising: transmitting, to an input device associated with the first device, information that instructs a user to input user information, and wherein the input device configured to output at least one of a light and a sound from an output apparatus of the input device in response to receiving the information.

19. A non-transitory computer-readable medium storing instructions executable by one or more computers, the instructions comprising:

one or more instructions for acquiring, from a plurality of devices worn by a plurality of users, location information indicating locations of the plurality of devices;

one or more instructions for selecting, in response to acquisition of a first measurement result including a first measurement time from a first measurement apparatus which measures a condition of a user wearing a device, a first device from the plurality of devices by comparing locations of the plurality of devices at the first measurement time with a location of the first measurement apparatus; and one or more instructions for storing the condition of a user measured by the first measurement apparatus in association with user identification information of the selected first device in a memory.

* * * * *